(12) United States Patent
Hoffmann et al.

(10) Patent No.: US 6,998,240 B2
(45) Date of Patent: Feb. 14, 2006

(54) SCREEN FOR SELECTIVE INHIBITORS OR ACTIVATORS OF SMAD PROTEIN FUNCTION

(75) Inventors: F. Michael Hoffmann, Madison, WI (US); Allen R. Comer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 545 days.

(21) Appl. No.: 10/166,917

(22) Filed: Jun. 11, 2002

(65) Prior Publication Data

US 2005/0164295 A1   Jul. 28, 2005

Related U.S. Application Data

(60) Provisional application No. 60/297,284, filed on Jun. 11, 2001.

(51) Int. Cl.
*G01N 33/53* (2006.01)
*C07K 14/00* (2006.01)

(52) U.S. Cl. ........................... 435/7.1; 530/350
(58) Field of Classification Search ........... 435/7.1; 530/350
See application file for complete search history.

(56) References Cited

U.S. PATENT DOCUMENTS 6,824,971 B1 * 11/2004 Pavletich et al. ............. 435/4

OTHER PUBLICATIONS

Akiyoshi et al. Dec. 3, 1999; J. Biol. Chem. 274(49): 35269-35277.*
Blanchette et al., 2001; J. Cellular Physiology 188: 264-273.*
Feng et al. 2000; EMBO J. 19(19): 5178-5193.*
Hua et al. Nov. 9, 1999; P.N.A.S. 96(23): 13130-13135.*
Kim et al. 2000; Genes & Development 14:1605-1616.*
Leong et al. May 25, 2000; J. Biol. Chem. 276(21): 18243-18248.*
Verrecchia et al. Sep. 29, 2000; J. Biol. Chem. 275(39): 30226-30231.*
von Bubnoff et al. 2001; Developmental Biology 239: 1-14.*
Akiyoshi, S., et al., J. Biol. Chem. 274:35269-25277, 1999.
de Caestecker, M.P., et al., J. Biol. Chem. 275:2115-22, 2000.
Chen, X. E., et al., Nature 389:85-9, 1997.
Colas, P., et al., Nature 380:548-550, 1996.
Dong, C., et al., Mol. Cell 5:27-34, 2000.
Feng, X.H., et al., EMBO J. 19:5178-5193, 2000.
Feng, X.H., et al., Genes Dev. 12:2153-2163, 1998.
Germain, S., et al., Genes Dev. 14:435-51, 2000.
Hata, A., et al., Genes Dev. 12:186-97, 1998.
Hua, X., et al., Proc. Natl. Acad. Sci. USA 96:13130-5, 1999.
Janknecht, R., et al., Genes Dev. 12:2114-9, 1998.
Kretzschmar, M., et al., Genes Dev. 13:806-16, 1999.
Liberati, N.T., et al., Proc. Natl. Acad. Sci. USA 96:4844-4849, 1999.
Luo, K., et al., Genes Dev. 13:2196-206, 1999.
Pardali, E., et al., J. Biol. Chem. 275:3552-60, 2000.
Park, B.J., et al., Cancer Res. 60:3031-3038, 2000.
Sano, Y., et al., J. Biol. Chem. 274:8949-57, 1999.
Shioda, T., et al., Proc. Natl. Acad. Sci. USA 95:9785-9790, 1998.
Souchelnytskyi, S., et al., J. Biol. Chem. 273:25364-70, 1998.
Sun, Y., et al., Mol. Cell 4:499-509, 1999.
Topper, J.N., et al., Proc. Natl. Acad. Sci. USA 95:9506-9511, 1998.
Tsukazaki, T., et al., Cell 95:779-91, 1998.
Wicks, S.J., et al., Mol. Cell. Biol. 20:8103-11, 2000.
Wotton, D., et al., Cell 97:29-39, 1999.
Xu, L., et al., Nat. Cell Biol. 2:559-562, 2000.
Yanagisaw, J., et al., Science 283:1317-1321, 1999.
Zhang, Y., et al., Nature 394:909-13, 1998.

* cited by examiner

*Primary Examiner*—Karen Cochrane Carlson
(74) *Attorney, Agent, or Firm*—Quarles & Brady LLP

(57) ABSTRACT

A method of screening for selective inhibitors or activators Smad protein function is disclosed. In one embodiment, the invention comprises the steps of (a) obtaining a phosphorylated Smad protein or protein complex, (b) allowing the phosphorylated Smad protein or complex to interact with a target protein or peptide in the presence of a test compound, and (c) analyzing the binding of the phosphorylated Smad complex or protein and the target protein or peptide, wherein a perturbation of binding indicates that the test compound is an inhibitor or activator of Smad-target protein interaction.

6 Claims, 9 Drawing Sheets

A

SDS-PAGE of Streptactin
Affinity Column Fractions
Stds 1 2 3 4 Total Lysate

B

Westerns
Anti-
Smad2+ Anti-
Anti-   Phospho
Smad4   Smad2

| | |
|---|---|
| Biotin- Fast R D-amide | Biotin – L D A L F Q G V P P N K S I Y D V W V S H P |
| HFAST-24mer R D-amide | L D A L F Q G V P P N K S I Y D V W V S H P |
| HFAST-24mer PP>AA R D-amide | L D A L F Q G V <u>A A</u> N K S I Y D V W V S H P |
| H-FAST-13mer | C F Q G V P P N K S I Y D V-amide |
| Biotin c-Jun T F-amide | Biotin – L K Q K V M N H V N S G C Q L M L T Q Q L Q |
| C-JUN 24mer T F-amide | L K Q K V M N H V N S G C Q L M L T Q Q L Q |
| CBP-23mer I-amide | A V E A A R Q I E R E A Q Q Q Q H L Y R V N |

FIG. 3

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1701
      (B) TYPE: nucleic acid
      (C) STRANDEDNESS: double
      (D) TOPOLOGY: linear (ii) MOLECULE TYPE: cDNA to mRNA
         ORIGINAL SOURCE:
         ORGANISM: Homo sapiens
         STRAIN: THP-1 cell
         CELL TYPE: monocytic cell (xi) SEQUENCE DESCRIPTION: SEQ ID NO:1:

```
AAGGAGCACA GTTCCAGGCG GGGCTGAGCT AGGGCGTAGC TGTGATTTCA GGGGCACCTC    60

TGGCGGCTGC CGTGATTTGA GAATCTCGGG TCTCTTGGCT GACTGATCCT GGGAGACTGT   120

GG ATG AAT AAT GCT GGG CAC GGC CCC ACC CGG AGG CTG CGA GGC TTG      167
   Met Asn Asn Ala Gly His Gly Pro Thr Arg Arg Leu Arg Gly Leu
   1               5                   10                  15

GGG GTC CTG GCC GGG GTG GCT CTG CTC GCT GCC CTC TGG CTC CTG TGG     215
Gly Val Leu Ala Gly Val Ala Leu Leu Ala Ala Leu Trp Leu Leu Trp
                20                  25                  30

CTG CTG GGG TCA GCC CCT CGG GGT ACC CCG GCA CCC CAG CCC ACG ATC     263
Leu Leu Gly Ser Ala Pro Arg Gly Thr Pro Ala Pro Gln Pro Thr Ile
            35                  40                  45

ACC ATC CTT GTC TGG CAC TGG CCC TTC ACT GAC CAG CCC CCA GAG CTG     311
Thr Ile Leu Val Trp His Trp Pro Phe Thr Asp Gln Pro Pro Glu Leu
        50                  55                  60

CCC AGC GAC ACC TGC ACC CGC TAC GGC ATC GCC CGC TGC CAC CTG AGT     359
Pro Ser Asp Thr Cys Thr Arg Tyr Gly Ile Ala Arg Cys His Leu Ser
65                  70                  75

GCC AAC CGA AGC CTG CTG GCC AGC GCC GAC GCC GTG GTC TTC CAC CAC     407
Ala Asn Arg Ser Leu Leu Ala Ser Ala Asp Ala Val Val Phe His His
80                  85                  90                  95

CGC GAG CTG CAG ACC CGG CGG TCC CAC CTG CCC CTG GCC CAG CGG CCG     455
Arg Glu Leu Gln Thr Arg Arg Ser His Leu Pro Leu Ala Gln Arg Pro
                100                 105                 110

CGA GGG CAG CCC TGG GTG TGG GCC TCC ATG GAG TCT CCT AGC CAC ACC     503
Arg Gly Gln Pro Trp Val Trp Ala Ser Met Glu Ser Pro Ser His Thr
            115                 120                 125

CAC GGC CTC AGC CAC CTC CGA GGC ATC TTC AAC TGG GTG CTG AGC TAC     551
His Gly Leu Ser His Leu Arg Gly Ile Phe Asn Trp Val Leu Ser Tyr
        130                 135                 140

CGG CGC GAC TCG GAC ATC TTT GTG CCC TAT GGC CGC CTG GAG CCC CAC     599
Arg Arg Asp Ser Asp Ile Phe Val Pro Tyr Gly Arg Leu Glu Pro His
145                 150                 155

TGG GGG CCC TCG CCA CCG CTG CCA GCC AAG AGC AGG GTG GCC GCC TGG     647
Trp Gly Pro Ser Pro Pro Leu Pro Ala Lys Ser Arg Val Ala Ala Trp
160                 165                 170                 175

GTG GTC AGC AAC TTC CAG GAG CGG CAG CTG CGT GCC AGG CTG TAC CGG     695
Val Val Ser Asn Phe Gln Glu Arg Gln Leu Arg Ala Arg Leu Tyr Arg
                180                 185                 190

CAG CTG GCG CCT CAT CTG CGG GTG GAT GTC TTT GGC CGT GCC AAT GGA     743
Gln Leu Ala Pro His Leu Arg Val Asp Val Phe Gly Arg Ala Asn Gly
            195                 200                 205

CGG CCA CTG TGC GCC AGC TGC CTG GTG CCC ACC GTG GCC CAG TAC CGC     791
Arg Pro Leu Cys Ala Ser Cys Leu Val Pro Thr Val Ala Gln Tyr Arg
        210                 215                 220

TTC TAC CTG TCC TTT GAG AAC TCT CAG CAC CGC GAC TAC ATT ACG GAG     839
Phe Tyr Leu Ser Phe Glu Asn Ser Gln His Arg Asp Tyr Ile Thr Glu
225                 230                 235

AAA TTC TGG CGC AAC GCA CTG GTG GCT GGC ACT GTG CCA GTG GTG CTG     887
Lys Phe Trp Arg Asn Ala Leu Val Ala Gly Thr Val Pro Val Val Leu
240                 245                 250                 255

GGG CCC CCA CGG GCC ACC TAT GAG GCC TTC GTG CCG GCT GAC GCC TTC     935
Gly Pro Pro Arg Ala Thr Tyr Glu Ala Phe Val Pro Ala Asp Ala Phe
                260                 265                 270

GTG CAT GTG GAT GAC TTT GGC TCA GCC CGA GAG CTG GCG GCT TTC CTC     983
Val His Val Asp Asp Phe Gly Ser Ala Arg Glu Leu Ala Ala Phe Leu
            275                 280                 285
```

```
ACT GGC ATG AAT GAG AGC CGA TAC CAA CGC TTC TTT GCC TGG CGT GAC    1031
Thr Gly Met Asn Glu Ser Arg Tyr Gln Arg Phe Phe Ala Trp Arg Asp
        290             295             300

AGG CTC CGC GTG CGA CTG TTC ACC GAC TGG CGG GAA CGT TTC TGT GCC    1079
Arg Leu Arg Val Arg Leu Phe Thr Asp Trp Arg Glu Arg Phe Cys Ala
        305             310             315

ATC TGT GAC CGC TAC CCA CAC CTA CCC CGC AGC CAA GTC TAT GAG GAC    1127
Ile Cys Asp Arg Tyr Pro His Leu Pro Arg Ser Gln Val Tyr Glu Asp
320             325             330             335

CTT GAG GGT TGG TTT CAG GCC TGA GATCCGCTGG CCGGGGGAGG TGGGTGTGGG    1181
Leu Glu Gly Trp Phe Gln Ala TER
            340         342

TGGAAGGGCT GGGTGTCGAA ATCAAACCAC CAGGCATCCG GCCCTTACCG GCAAGCAGCG    1241

GGCTAACGGG AGGCTGGGCA CAGAGGTCAG GAAGCAGGGG TGGGGGGTGC AGGTGGGCAC    1301

TGGAGCATGC AGAGGAGGTG AGAGTGGGAG GGAGGTAACG GGTGCCTGCT GCGGCAGACG    1361

GGAGGGGAAA GGCTGCCGAG GACCCTCCCC ACCCTGAACA AATCTTGGGT GGGTGAAGGC    1421

CTGGCTGGAA GAGGGTGAAA GGCAGGGCCC TTGGGGCTGG GGGGCACCCC AGCCTGAAGT    1481

TTGTGGGGGC CAAACCTGGG ACCCCGAGCT TCCTCGGTAG CAGAGGCCCT GTGGTCCCCG    1541

AGACACAGGC ACGGGTCCCT GCCACGTCCA TAGTTCTGAG GTCCCTGTGT GTAGGCTGGG    1601

GCGGGGCCCA GGAGACCACG GGGAGCAAAC CAGCTTGTTC TGGGCTCAGG GAGGGAGGGC    1661

GGTGGACAAT AAACGTCTGA GCAGTGAAAA AAAAAAAAA                          1701

(2) INFORMATION FOR SEQ ID NO:2:

(i) SEQUENCE CHARACTERISTICS:
        (A) LENGTH: 342
        (B) TYPE: amino acid
        (D) TOPOLOGY: linear (ii) MOLECULE TYPE: protein
            ORIGINAL SOURCE:
                ORGANISM: Homo sapiens
                STRAIN: THP-1 cell
                CELL TYPE: monocytic cell (xi) SEQUENCE DESCRIPTION: SEQ ID NO:2:

Met Asn Asn Ala Gly His Gly Pro Thr Arg Arg Leu Arg Gly Leu
1               5               10              15

Gly Val Leu Ala Gly Val Ala Leu Leu Ala Ala Leu Trp Leu Leu
                20              25              30

Trp Leu Leu Gly Ser Ala Pro Arg Gly Thr Pro Ala Pro Gln Pro
                35              40              45

Thr Ile Thr Ile Leu Val Trp His Trp Pro Phe Thr Asp Gln Pro
                50              55              60

Pro Glu Leu Pro Ser Asp Thr Cys Thr Arg Tyr Gly Ile Ala Arg
                65              70              75

Cys His Leu Ser Ala Asn Arg Ser Leu Leu Ala Ser Ala Asp Ala
                80              85              90

Val Val Phe His His Arg Glu Leu Gln Thr Arg Arg Ser His Leu
                95              100             105

Pro Leu Ala Gln Arg Pro Arg Gly Gln Pro Trp Val Trp Ala Ser
                110             115             120

Met Glu Ser Pro Ser His Thr His Gly Leu Ser His Leu Arg Gly
                125             130             135

Ile Phe Asn Trp Val Leu Ser Tyr Arg Arg Asp Ser Asp Ile Phe
                140             145             150
```

```
                                    -continued

Val Pro Tyr Gly Arg Leu Glu Pro His Trp Gly Pro Ser Pro Pro
                155                 160                 165

Leu Pro Ala Lys Ser Arg Val Ala Ala Trp Val Ser Asn Phe
                170                 175                 180

Gln Glu Arg Gln Leu Arg Ala Arg Leu Tyr Arg Gln Leu Ala Pro
                185                 190                 195

His Leu Arg Val Asp Val Phe Gly Arg Ala Asn Gly Arg Pro Leu
                200                 205                 210

Cys Ala Ser Cys Leu Val Pro Thr Val Ala Gln Tyr Arg Phe Tyr
                215                 220                 225

Leu Ser Phe Glu Asn Ser Gln His Arg Asp Tyr Ile Thr Glu Lys
                230                 235                 240

Phe Trp Arg Asn Ala Leu Val Ala Gly Thr Val Pro Val Val Leu
                245                 250                 255

Gly Pro Pro Arg Ala Thr Tyr Glu Ala Phe Val Pro Ala Asp Ala
                260                 265                 270

Phe Val His Val Asp Asp Phe Gly Ser Ala Arg Glu Leu Ala Ala
                275                 280                 285

Phe Leu Thr Gly Met Asn Glu Ser Arg Tyr Gln Arg Phe Phe Ala
                290                 295                 300

Trp Arg Asp Arg Leu Arg Val Arg Leu Phe Thr Asp Trp Arg Glu
                305                 310                 315

Arg Phe Cys Ala Ile Cys Asp Arg Tyr Pro His Leu Pro Arg Ser
                320                 325                 330

Gln Val Tyr Glu Asp Leu Glu Gly Trp Phe Gln Ala
                335                 340     342

(2) INFORMATION FOR SEQ ID NO:3:

(i) SEQUENCE CHARACTERISTICS:
        (A) LENGTH: 52
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:3:

TCGACAAGCT TGATATCGGC CTGTGAGGCC TCACTGGCCG CGGCCGCGGT AC         52

(2) INFORMATION FOR SEQ ID NO:4:

(i) SEQUENCE CHARACTERISTICS:
        (A) LENGTH: 44
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:4:

GTTCGAACTA TAGCCGGACA CTCCGGAGTG ACCGGCGCCG GCGC                   44

(2) INFORMATION FOR SEQ ID NO:5:

(i) SEQUENCE CHARACTERISTICS:
        (A) LENGTH: 11
        (B) TYPE: nucleic acid
        (C) STRANDEDNESS: double
        (D) TOPOLOGY: linear
```

-continued (ii) MOLECULE TYPE: other nucleic acid, synthetic DNA (xi) SEQUENCE DESCRIPTION: SEQ ID NO:5:

| CTTTAGAGCA C | 11 |
|---|---|

(2) INFORMATION FOR SEQ ID NO:6:

(i) SEQUENCE CHARACTERISTICS:
        (A) LENGTH: 1766
        (B) TYPE: nucleic acid
        (C) STRANDEDNESS: double
        (D) TOPOLOGY: linear (ii) MOLECULE TYPE: cDNA to mRNA
        ORIGINAL SOURCE:
        ORGANISM: Homo sapiens
        STRAIN: WM266-4 cell
        CELL TYPE: melanoma (xi) SEQUENCE DESCRIPTION: SEQ ID NO:6:

| CGGTCAGGTC CAGCACTTGG GAGCTGACTG TGCTGGAGGT GACAGGCTTT GCGGGGTCCG | 60 |
|---|---|
| CCTGTGTGCA GGAGTCGCAA GGTCGCTGAG CAGGACCCAA AGGTGGCCCG AGGCAGCCGG | 120 |

| GATGACAGCT CTCCCCAGGA ATCCTGCTGC CTGCTGAGAA AC ATG GTC AGC AAG | 174 |
|---|---|
|                                                                                    Met Val Ser Lys | |
|                                                                                     1 | |
| TCC CGC TGG AAG CTC CTG GCC ATG TTG GCT CTG GTC CTG GTC GTC ATG | 222 |
| Ser Arg Trp Lys Leu Leu Ala Met Leu Ala Leu Val Leu Val Val Met | |
| 5                  10                  15                  20 | |
| GTG TGG TAT TCC ATC TCC CGG GAA GAC AGT TTT TAT TTT CCC ATC CCA | 270 |
| Val Trp Tyr Ser Ile Ser Arg Glu Asp Ser Phe Tyr Phe Pro Ile Pro | |
|                         25                  30                  35 | |
| GAG AAG AAG GAG CCG TGC CTC CAG GGT GAG GCA GAG AGC AAG GCC TCT | 318 |
| Glu Lys Lys Glu Pro Cys Leu Gln Gly Glu Ala Glu Ser Lys Ala Ser | |
|                    40                  45                  50 | |
| AAG CTC TTT GGC AAC TAC TCC CGG GAT CAG CCC ATC TTC CTG CGG CTT | 366 |
| Lys Leu Phe Gly Asn Tyr Ser Arg Asp Gln Pro Ile Phe Leu Arg Leu | |
|             55                  60                  65 | |
| GAG GAT TAT TTC TGG GTC AAG ACG CCA TCT GCT TAC GAG CTG CCC TAT | 414 |
| Glu Asp Tyr Phe Trp Val Lys Thr Pro Ser Ala Tyr Glu Leu Pro Tyr | |
| 70                  75                  80 | |
| GGG ACC AAG GGG AGT GAG GAT CTG CTC CTC CGG GTG CTA GCC ATC ACC | 462 |
| Gly Thr Lys Gly Ser Glu Asp Leu Leu Leu Arg Val Leu Ala Ile Thr | |
| 85                  90                  95                  100 | |
| AGC TCC TCC ATC CCC AAG AAC ATC CAG AGC CTC AGG TGC CGC CGC TGT | 510 |
| Ser Ser Ser Ile Pro Lys Asn Ile Gln Ser Leu Arg Cys Arg Arg Cys | |
|                    105                 110                 115 | |
| GTG GTC GTG GGG AAC GGG CAC CGG CTG CGG AAC AGC TCA CTG GGA GAT | 558 |
| Val Val Val Gly Asn Gly His Arg Leu Arg Asn Ser Ser Leu Gly Asp | |
|                    120                 125                 130 | |
| GCC ATC AAC AAG TAC GAT GTG GTC ATC AGA TTG AAC AAT GCC CCA GTG | 606 |
| Ala Ile Asn Lys Tyr Asp Val Val Ile Arg Leu Asn Asn Ala Pro Val | |
|             135                  140                 145 | |
| GCT GGC TAT GAG GGT GAC GTG GGC TCC AAG ACC ACC ATG CGT CTC TTC | 654 |
| Ala Gly Tyr Glu Gly Asp Val Gly Ser Lys Thr Thr Met Arg Leu Phe | |
|             150                  155                 160 | |
| TAC CCT GAA TCT GCC CAC TTC GAC CCC AAA GTA GAA AAC AAC CCA GAC | 702 |
| Tyr Pro Glu Ser Ala His Phe Asp Pro Lys Val Glu Asn Asn Pro Asp | |
| 165                  170                 175                 180 | |
| ACA CTC CTC GTC CTG GTA GCT TTC AAG GCA ATG GAC TTC CAC TGG ATT | 750 |
| Thr Leu Leu Val Leu Val Ala Phe Lys Ala Met Asp Phe His Trp Ile | |
|                    185                 190                 195 | |

```
GAG ACC ATC CTG AGT GAT AAG AAG CGG GTG CGA AAG GGT TTC TGG AAA        798
Glu Thr Ile Leu Ser Asp Lys Lys Arg Val Arg Lys Gly Phe Trp Lys
            200                 205                 210

CAG CCT CCC CTC ATC TGG GAT GTC AAT CCT AAA CAG ATT CGG ATT CTC        846
Gln Pro Pro Leu Ile Trp Asp Val Asn Pro Lys Gln Ile Arg Ile Leu
            215                 220                 225

AAC CCC TTC TTC ATG GAG ATT GCA GCT GAC AAA CTG CTG AGC CTG CCA        894
Asn Pro Phe Phe Met Glu Ile Ala Ala Asp Lys Leu Leu Ser Leu Pro
        230                 235                 240

ATG CAA CAG CCA CGG AAG ATT AAG CAG AAG CCC ACC ACG GGC CTG TTG        942
Met Gln Gln Pro Arg Lys Ile Lys Gln Lys Pro Thr Thr Gly Leu Leu
245                 250                 255                 260

GCC ATC ACG CTG GCC CTC CAC CTC TGT GAC TTG GTG CAC ATT GCC GGC        990
Ala Ile Thr Leu Ala Leu His Leu Cys Asp Leu Val His Ile Ala Gly
                265                 270                 275

TTT GGC TAC CCA GAC GCC TAC AAC AAG AAG CAG ACC ATT CAC TAC TAT       1038
Phe Gly Tyr Pro Asp Ala Tyr Asn Lys Lys Gln Thr Ile His Tyr Tyr
                280                 285                 290

GAG CAG ATC ACG CTC AAG TCC ATG GCG GGG TCA GGC CAT AAT GTC TCC       1086
Glu Gln Ile Thr Leu Lys Ser Met Ala Gly Ser Gly His Asn Val Ser
                295                 300                 305

CAA GAG GCC CTG GCC ATT AAG CGG ATG CTG GAG ATG GGA GCT ATC AAG       1134
Gln Glu Ala Leu Ala Ile Lys Arg Met Leu Glu Met Gly Ala Ile Lys
310                 315                 320

AAC CTC ACG TCC TTC TGA CCTGGGCAAG AGCTGTAGCC TGTCGGTTGC              1182
Asn Leu Thr Ser Phe TER
325                 329

CTACTCTGCT GTCTGGGTGA CCCCCATGCG TGGCTGTGGG GGTGGCTGGT GCCAGTATGA     1242

CCCACTTGGA CTCACCCCCT CTTGGGGAGG GAGTTCTGGG CCTGGCCAGG TCTGAGATGA     1302

GGCCATGCCC CTGGCTGCTC TTATGGAGCC GAGATCCAGT CAGGGTGGGG GCGCTGGAGC     1362

CGTGGGAGCC CGGCCAGGGC AGGGGGCTCG TCGCTGTGGC ACCCCCTCTC TGCCAGCACC     1422

AAGAGATTAT TTAATGGGCT ATTTAATTAA GGGGTAGGAA GGTGCTGTGG GCTGGTCCCA     1482

CACATCCAGG AAAGAGGCCA GTAGAGAATT CTGCCCACTT TTTATAAAAA CTTACAGCGA     1542

TGGCCCCACC AAGGCCTAGA CACGGCACTG GCCTCCCAGG AGGGCAGGGG CATTGGGAAT     1602

GGGTGGGTGC CCTCCAGAGA GGGGCTGCTA CCTCCCAGCA GGCATGGGAA GAGCACTGGT     1662

GTGGGGGTTC CACCGAGAAG GGGACCTCAT CTAGAAAAGA GGTTACAAAC CTACCATTAA     1722

ACTATTTTTC CTAAAACGGA AAAAAAAAAA AAAAAAAAA AAAA                      1766

(2) INFORMATION FOR SEQ ID NO:7:

(i) SEQUENCE CHARACTERISTICS:
        (A) LENGTH: 44
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION:  SEQ ID NO:7:

CTCTCCGATA TCTGTTTTAT TTTCCCATCC CAGAGAAGAA GGAG                        44

(2) INFORMATION FOR SEQ ID NO:8:

(i) SEQUENCE CHARACTERISTICS:
        (A) LENGTH: 36
        (B) TYPE: nucleic acid
        (C) STRANDEDNESS: double
        (D) TOPOLOGY: linear
```

-continued (ii) MOLECULE TYPE: other nucleic acid, synthetic DNA (xi) SEQUENCE DESCRIPTION: SEQ ID NO:8:

GATTAAGGTA CCAGGTCAGA AGGACGTGAG GTTCTT        36

(2) INFORMATION FOR SEQ ID NO:9:

(i) SEQUENCE CHARACTERISTICS:
       (A) LENGTH: 2232
       (B) TYPE: nucleic acid
       (C) STRANDEDNESS: double
       (D) TOPOLOGY: linear (ii) MOLECULE TYPE: cDNA to mRNA
        ORIGINAL SOURCE:
        ORGANISM: Homo sapiens
        STRAIN: WM266-4 cell
        CELL TYPE: melanoma (xi) SEQUENCE DESCRIPTION: SEQ ID NO:9:

```
CGCGTTGTGG GCTCCCGCCG GGGTCCCCCG CGGCTGTCGC CGCCGCCTAC GCCGCTGCCT        60

CCGCCTTCCT GCCCCGCGTC GGGCCGGGCG CCACCTCCCC CCTGCCTCCC TCTCCGCTGT       120

GGTCATTTAG GAAATCGTAA ATCATGTGAA G ATG GGA CTC TTG GTA TTT GTG          172
                                   Met Gly Leu Leu Val Phe Val
                                    1               5

CGC AAT CTG CTG CTA GCC CTC TGC CTC TTT CTG GTA CTG GGA TTT TTG        220
Arg Asn Leu Leu Leu Ala Leu Cys Leu Phe Leu Val Leu Gly Phe Leu
         10                  15                  20

TAT TAT TCT GCG TGG AAG CTA CAC TTA CTC CAG TGG GAG GAG GAC TCC        268
Tyr Tyr Ser Ala Trp Lys Leu His Leu Leu Gln Trp Glu Glu Asp Ser
 25                  30                  35

AAT TCA GTG GTT CTT TCC TTT GAC TCC GCT GGA CAA ACA CTA GGC TCA        316
Asn Ser Val Val Leu Ser Phe Asp Ser Ala Gly Gln Thr Leu Gly Ser
 40                  45                  50                  55

GAG TAT GAT CGG TTG GGC TTC CTC CTG AAT CTG GAC TCT AAA CTG CCT        364
Glu Tyr Asp Arg Leu Gly Phe Leu Leu Asn Leu Asp Ser Lys Leu Pro
                 60                  65                  70

GCT GAA TTA GCC ACC AAG TAC GCA AAC TTT TCA GAG GGA GCT TGC AAG        412
Ala Glu Leu Ala Thr Lys Tyr Ala Asn Phe Ser Glu Gly Ala Cys Lys
             75                  80                  85

CCT GGC TAT GCT TCA GCC TTG ATG ACG GCC ATC TTC CCC CGG TTC TCC        460
Pro Gly Tyr Ala Ser Ala Leu Met Thr Ala Ile Phe Pro Arg Phe Ser
         90                  95                 100

AAG CCA GCA CCC ATG TTC CTG GAT GAC TCC TTT CGC AAG TGG GCT AGA        508
Lys Pro Ala Pro Met Phe Leu Asp Asp Ser Phe Arg Lys Trp Ala Arg
105                 110                 115

ATC CGG GAG TTC GTG CCG CCT TTT GGG ATC AAA GGT CAA GAC AAT CTG        556
Ile Arg Glu Phe Val Pro Pro Phe Gly Ile Lys Gly Gln Asp Asn Leu
120                 125                 130                 135

ATC AAA GCC ATC TTG TCA GTC ACC AAA GAG TAC CGC CTG ACC CCT GCC        604
Ile Lys Ala Ile Leu Ser Val Thr Lys Glu Tyr Arg Leu Thr Pro Ala
                140                 145                 150

TTG GAC AGC CTC CGC TGC CGC CGC TGC ATC ATC GTG GGC AAT GGA GGC        652
Leu Asp Ser Leu Arg Cys Arg Arg Cys Ile Ile Val Gly Asn Gly Gly
            155                 160                 165

GTT CTT GCC AAC AAG TCT CTG GGG TCA CGA ATT GAC GAC TAT GAC ATT        700
Val Leu Ala Asn Lys Ser Leu Gly Ser Arg Ile Asp Asp Tyr Asp Ile
        170                 175                 180

GTG GTG AGA CTG AAT TCA GCA CCA GTG AAA GGC TTT GAG AAG GAC GTG        748
Val Val Arg Leu Asn Ser Ala Pro Val Lys Gly Phe Glu Lys Asp Val
    185                 190                 195
```

```
GGC AGC AAA ACG ACA CTG CGC ATC ACC TAC CCC GAG GGC GCC ATG CAG        796
Gly Ser Lys Thr Thr Leu Arg Ile Thr Tyr Pro Glu Gly Ala Met Gln
200             205                 210                 215

CGG CCT GAG CAG TAC GAG CGC GAT TCT CTC TTT GTC CTC GCC GGC TTC        844
Arg Pro Glu Gln Tyr Glu Arg Asp Ser Leu Phe Val Leu Ala Gly Phe
                220                 225                 230

AAG TGG CAG GAC TTT AAG TGG TTG AAA TAC ATC GTC TAC AAG GAG AGA        892
Lys Trp Gln Asp Phe Lys Trp Leu Lys Tyr Ile Val Tyr Lys Glu Arg
            235                 240                 245

GTG AGT GCA TCG GAT GGC TTC TGG AAA TCT GTG GCC ACT CGA GTG CCC        940
Val Ser Ala Ser Asp Gly Phe Trp Lys Ser Val Ala Thr Arg Val Pro
        250                 255                 260

AAG GAG CCC CCT GAG ATT CGA ATC CTC AAC CCA TAT TTC ATC CAG GAG        988
Lys Glu Pro Pro Glu Ile Arg Ile Leu Asn Pro Tyr Phe Ile Gln Glu
    265                 270                 275

GCC GCC TTC ACC CTC ATT GGC CTG CCC TTC AAC AAT GGC CTC ATG GGC       1036
Ala Ala Phe Thr Leu Ile Gly Leu Pro Phe Asn Asn Gly Leu Met Gly
280                 285                 290                 295

CGG GGG AAC ATC CCT ACC CTT GGC AGT GTG GCA GTG ACC ATG GCA CTA       1084
Arg Gly Asn Ile Pro Thr Leu Gly Ser Val Ala Val Thr Met Ala Leu
                300                 305                 310

CAC GGC TGT GAC GAG GTG GCA GTC GCA GGA TTT GGC TAT GAC ATG AGC       1132
His Gly Cys Asp Glu Val Ala Val Ala Gly Phe Gly Tyr Asp Met Ser
                315                 320                 325

ACA CCC AAC GCA CCC CTG CAC TAC TAT GAG ACC GTT CGC ATG GCA GCC       1180
Thr Pro Asn Ala Pro Leu His Tyr Tyr Glu Thr Val Arg Met Ala Ala
            330                 335                 340

ATC AAA GAG TCC TGG ACG CAC AAT ATC CAG CGA GAG AAA GAG TTT CTG       1228
Ile Lys Glu Ser Trp Thr His Asn Ile Gln Arg Glu Lys Glu Phe Leu
        345                 350                 355

CGG AAG CTG GTG AAA GCT CGC GTC ATC ACT GAT CTA AGC AGT GGC ATC       1276
Arg Lys Leu Val Lys Ala Arg Val Ile Thr Asp Leu Ser Ser Gly Ile
360                 365                 370                 375

TGA GTGGGCCCAG CACATGGCCA TAGAGGCCCA GCACCACCA GGAGCAGCAG             1329
TER

CCAGCACCAC CTACACAGGA GTCTTCAGAC CCAGAGAAGG ACGGTGCCAA GGGCCCCAGG     1389

GGCAGCAAGG CCTTGGTGGA GCAGCCAGAG CTGTGCCTGC TCAGCAGCCA GTCTCAGAGA     1449

CCAGCACTCA GCCTCATTCA GCATGGGTCC TTGATGCCAG AGGGCCAGCA GGCTCCTGGC     1509

TGTGCCCAGC AGGCCCAGCA TGCAGGTGGT GGGACACTGG GCAGCAAGGC TGCTGCCGGA     1569

ATCACTTCTC CAATCAGTGT TTGGTGTATT ATCATTTTGT GAATTGGGT AGGGGGGAGG     1629

GTAGGGATAA TTTATTTTTA AATAAGGTTG GAGATGTCAA GTTGGGTTCA CTTGCCATGC     1689

AGGAAGAGGC CCACTAGAGG GCCCATCAGG CAGTGTTACC TGTTAGCTCC CTGTGGGGCA     1749

GGAGTGCCAG GACCAGCCTG TACCTTGCTG TGGGGCTACA GGATGGTGGG CAGGATCTCA     1809

AGCCAGCCCC CTCCAGCTCA TGACACTGTT TGGCCTTTCT TGGGGAGAAG GCGGGGTATT     1869

CCCACTCACC AGCCCTAGCT GTCCCATGGG GAAACCCTGG AGCCATCCCT TCGGAGCCAA     1929

CAAGACCGCC CCAGGGCTAT AGCAGAAAGA ACTTTAAAGC TCAGGAGGGT GACGCCCAGC     1989

TCCGCCTGCT GGGAAGAGCT CCCCTCCACA GCTGCAGCTG ATCCATAGGA CTACCGCAGG     2049

CCCGGACTCA CCAACTTGCC ACATGTTCTA GGTTTCAGCA ACAAGACTGC CAGGTGGTTG     2109

GGTTCTGCCT TTAGCCTGGA CCAAAGGGAA GTGAGGCCCA AGGAGCTTAC CCAAGCTGTG     2169

GCAGCCGTCC CAGGCCACCC CCATGGAAGC AATAAAGCTC TTCCCTGTAA AAAAAAAAA     2229

AAA                                                                   2232
```

(2) INFORMATION FOR SEQ ID NO:10:

(i) SEQUENCE CHARACTERISTICS:
        (A) LENGTH: 38
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:10:

CTCTGTAGGC CTTACTCCAG TGGGAGGAGG ACTCCAAT                  38

(2) INFORMATION FOR SEQ ID NO:11:

(i) SEQUENCE CHARACTERISTICS:
        (A) LENGTH: 37
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:11:

GACTCAGGTA CCACTCAGAT GCCACTGCTT AGATCAG                   37

(2) INFORMATION FOR SEQ ID NO:12:

(i) SEQUENCE CHARACTERISTICS:
        (A) LENGTH: 34
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:12:

CTCTCGGATA TCCCACTGTG TACCCTAATG GGTC                        34

(2) INFORMATION FOR SEQ ID NO:13:

(i) SEQUENCE CHARACTERISTICS:
        (A) LENGTH: 36
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:13:

GTAGACGCGG CCGCTCAGGT GAACCAAGCC GCTATG                    36

(2) INFORMATION FOR SEQ ID NO:14:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:14:

CGCCAGTCCT CCGATTGACT GAGT                                 24

(2) INFORMATION FOR SEQ ID NO:15:

(i) SEQUENCE CHARACTERISTICS:
        (A) LENGTH: 31
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:15:

```
CCATGGTACC TGTGCTGTCT GGGAAGCGGG A                              31
```

(2) INFORMATION FOR SEQ ID NO:16:

(i) SEQUENCE CHARACTERISTICS:
        (A) LENGTH: 40
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:16:

```
AAGTATAAGC TTCCATGGAT GATGATATCG CCGCGCTCGT                     40
```

(2) INFORMATION FOR SEQ ID NO:17:

(i) SEQUENCE CHARACTERISTICS:
        (A) LENGTH: 40
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:17:

```
ATTTAAGGTA CCGAAGCATT TGCGGTGGAC GATGGAGGGG                     40
```

(2) INFORMATION FOR SEQ ID NO:18:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:18:

```
CACCTCCGAG GCATCTTCAA CTG                                       23
```

(2) INFORMATION FOR SEQ ID NO:19:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:19:

```
CGTTGGTATC GGCTCTCATT CATG                                      24
```

-continued (2) INFORMATION FOR SEQ ID NO:20:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:20:

GATATCGCCG CGCTCGTCGT CGAC        24

(2) INFORMATION FOR SEQ ID NO:21:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:21:

CAGGAAGGAA GGCTGGAAGA GTGC        24

SCREEN FOR SELECTIVE INHIBITORS OR ACTIVATORS OF SMAD PROTEIN FUNCTION

CROSS-REFERENCE TO RELATED APPLICATION

This application claims priority to U.S. Ser. No. 60/297,284, filed Jun. 11, 2001 which is incorporated by reference herein.

STATEMENT REGARDING FEDERALLY SPONSORED RESEARCH AND DEVELOPMENT

This invention was made with United States government support awarded by the following agencies: NIH RR06610. The United States has certain rights in this invention.

BACKGROUND OF THE INVENTION

The TGFβ Pathway

TGFβs are secreted polypeptides that are critical inhibitors of epithelial growth, immune and hematopoietic functions and activators of connective tissue growth (reviewed by Massague, J. and Y. G. Chen, *Genes Dev.* 14:627–44, 2000). TGFβ1, 2, and 3 are three members of the large TGFβ superfamily that also includes the bone morphogenetic proteins, the growth and differentiation factors (GDFs), nodal-related proteins and activins. TGFβs signal by activating two receptor serine/threonine protein kinases, the Type I and Type II receptors. The receptors phosphorylate Smad2 and Smad3 which form a heteromeric complex with Smad4 and translocate into the nucleus. The phosphorylated Smad complex (Smad-P) regulates transcription by interactions with several DNA binding proteins, transcriptional co-activator proteins and transcriptional repressor proteins. The signal is terminated by multi-ubiquitination of Smad and proteasome-mediated degradation (Lo, R. S. and J. Massague, *Nat. Cell. Biol.* 1:472–478, 1999).

The Smad proteins are key components of TGFββ signal transduction, carrying the signal into the nucleus and generating a diverse set of tissue-specific responses. Smad proteins have an N-terminal globular domain with DNA binding activity, a central linker region with regulatory sites, and a C-terminal globular domain with transcriptional regulatory activity (Liu, F., et al., *Genes Dev.* 11:3157–67, 1997; Liu, F., et al., *Nature* 381:620–3, 1996). Both the N-terminal and C-terminal domain structures have been solved by X-ray crystallography (Shi, Y., et al., *Cell* 94:585–94, 1998; Shi, Y., et al., *Nature* 388:87–93, 1997). The DNA binding activity is associated with a hairpin loop in the N-terminal domain. The DNA binding activity is probably not the basis of the selectivity since all Smads recognize the same sequence, CAGAC (Shi, Y., et al., supra, 1998). The DNA-binding activity of Smads is also low-affinity and probably plays a role only in the context of Smad association with other DNA binding proteins such as FAST, Mixer, Milk, AP-1, TFE-3, and AML (Chen, X., E., et al., *Nature* 389:85–9, 1997; Germain, S., et al., *Genes Dev.* 14:435–51, 2000; Zhang, Y., et al., *Nature* 394:909–13, 1998; Hua, X., et al., *Proc. Natl. Acad. Sci. USA* 96:13130–5, 1999; Pardali, E., et al., *J. Biol. Chem.* 275:3552–60, 2000). The specific interactions of Smad and the Type I receptor are dictated by the L3 loop in Smad and the L4,5 loop in the Type I receptor (Lo, R. S., et al., *EMBO J.* 17:996–1005, 1998). A specific alpha helical structure in the Smad C-terminal domain, αhelix-2, specifies the binding of Smad to the DNA binding protein FAST (Chen, Y. G., et al., *Genes Dev.* 12:2144–52, 1998). Smad-P complexes also recruit the transcriptional co-activators p300/CBP and the transcriptional co-repressors TGIF, c-Ski and Sno-N to promoters bound by Smad-DNA binding protein complexes. p300/CBP has intrinsic histone acetyltransferase activity that can facilitate transcription; the co-repressors recruit histone deacetylases (Wotton, D., et al., *Cell* 97:29–39, 1999; Luo, K., et al., *Genes Dev.* 13:2196–206, 1999; Janknecht, R., et al., *Genes Dev.* 12:2114–9, 1998; de Caestecker, M. P., et al., *J. Biol. Chem.* 275:2115–22, 2000). Smad7 is an antagonistic Smad that inhibits Smad2 or 3 activation by binding to TGFβ Type I receptors (Souchelnytskyi, S., et al., *J. Biol. Chem.* 273:25364–70, 1998). A second antagonistic Smad, Smad6, regulates BMP signaling by competing with Smad4 to bind phosphorylated Smad1 (Hata, A., et al., *Genes Dev.* 12:186–97, 1998). Smad7 expression is increased by TGFβ and by other signals that negatively regulate TGFβ signaling, e.g., interferon γ, TNFα and interleukin 1β (Bitzer, M., et al., *Genes Dev.* 14:187–97, 2000).

Although Smad2 and Smad3 are both involved in mediating the response to TGFβ, they exhibit several functional differences. The N-terminal domain of Smad2 contains a short additional sequence that disrupts the DNA binding of the Smad2 N-terminal domain; the MH1 domain of Smad 3 can bind DNA. Smad2 interacts with FAST2 to activate transcription of the goosecoid promoter but Smad3 interaction with FAST2 suppresses transcription (Labbe, E., et al., *Mol. Cell* 2:109–20, 1998). Loss-of-function mutations in mice also exhibit different phenotypes. The unphosphorylated, cytoplasmic Smad proteins are also regulated by protein—protein interactions. SARA is a binding protein for Smad2 (but not Smad1) that facilitates phosphorylation of these Smads by the Type I receptor (Tsukazaki, T., et al., *Cell* 95:779–91, 1998). The cytoplasmic localization of Smad 2, 3, and 4 in epithelial cells may be due to association of these Smads with microtubules (Dong, C., et al., *Mol. Cell* 5:27–34, 2000).

TGFβ and Disease

There is an extensive literature on the role of TGFβ in a broad variety of human diseases including cancer (Akhurst, R. J. and A. Balmain, *J. Pathol.* 187:82–90, 1999; de Caestecker, M. P., et al., *J. Natl. Cancer Inst.* 92:1388–402, 2000; Taipale, J., et al., *Adv. Cancer Res.* 75:87–134, 1998), immunoregulation (Letterio, J. J. and A. B. Roberts, *Annu. Rev. Immunol.* 16:137–61, 1998), wound healing and tissue repair (Grande, J. P., *Proc. Soc. Exp. Biol. Med.* 214:27–40, 1997). As discussed by Akhurst and Balmain in their recent review, TGFβ has been implicated in tumor suppressor functions through its growth inhibitory properties on most epithelial and hematopoietic cell types. Loss-of-function mutations in TGFβ receptors and Smads allow cells to escape the grow-inhibitory functions of TGFβ. More indirect mechanisms, such as elevated mdm2, have also been proposed as ways that cells escape negative growth control (Sun, P., et al., *Science* 282:2270–2, p53-independent role of MDM2 in TGF-beta1 resistance.). And yet, as emphasized by Akhurst and Balmain, a more frequent role of TGFβ in cancer is to facilitate the progression and spread of tumor cells. Overexpression of TGFβ has been reported in advanced mouse and human carcinomas. The tumor-derived TGFβ can aid tumorigenicity by direct actions on the cancer cell, by induction of angiogenesis, by local or systemic immunosuppression, and by alterations of stromal tissue that facilitate invasiveness (Akhurst, R. J. and A. Balmain, supra, 1999).

Non-Smad Proteins Involved in TGF-β Signaling

Although the focus of the proposed screen disclosed below is on the critical Smad component of TGFβ signaling, it should be noted that there are other independent of the Smads. The role of these other pathways will be important to future design of combinatorial drug strategies for inhibition of TGFβ signaling, one component of which will be the Smad inhibitors to be identified by the proposed screens.

There are at least four different examples that illustrate how TGFβ mediated signal transduction processes are more complex than simple activation of Smads: (a) Negative regulation of Smad function by MAPK/ERK, (b) Positive regulation of Smad activation by MAPKK1, (c) Cooperative signaling initiated by TGFβ of both Smad and MAPK pathway activation, and (d) Smad-independent signaling by TGFβ.

One mechanism that is important to generating tissue-specific responses is cross-talk between the Smad pathway and other signaling pathways. Nuclear translocation of Smads is negatively regulated by MAPK phosphorylation of the Smad linker region (Kretzschmar, M., et al., *Genes Dev.* 13:804–16, 1999). Intracellular calcium levels can also negatively impact TGFβ signaling through $Ca^{++}$-calmodulin dependent protein kinase II. Cam kinase II phosphorylates Smad2 at several sites (serines 110, 240 and 260) in response to activation of several growth factor receptor signaling pathways including the HER2 oncoprotein (Wicks, S. J., et al., *Mol. Cell. Biol.* 20:8103–11, 2000).

There are not yet many examples of Smads being used by other signaling pathways, but MEKK-1 can activate Smad2 function in endothelial cells (Brown, J. D., et al., *J. Biol. Chem.* 274:8797–805, 1999). This result raises the possibility that Smads may be utilized by non-TGFβ signal transduction pathways.

There is evidence that TGFβ activates MAPK pathways, including the MKK4-JNK pathway in a human fibrosarcoma cell line (Hocevar, B. A., et al., *EMBO J.* 18:1345–56, 1999) and in the mink lung epithelial cell line Mv1Lu (Engel, M. E., et al., *J. Biol. Chem.* 274:37413–20, 1999). Although the precise molecular mechanism of MAPK-pathway activation by TGFβ receptors is not clear at this time, MAPKs can activate AP-1 and ATF2 transcription factors that act in concert, perhaps synergistically, with activated Smad-P at specific target promoters. Hocevar and colleagues report that inhibition of the MKK4-JNK pathway blocks TGFβ induction of fibronectin while having little effect on TGFβ induction of PAI-1. They propose that this specificity may be due to the requirement for c-jun-ATF2 heterodimers at the fibronectin promoter but not at the PAI-1 promoter (Hocevar, B. A., et al., supra, 1999).

Mulder and colleagues have reported on the rapid activation of Ras during TGFβ upregulation of Cdk inhibitors ($p27^{Kip1}$ and $p21^{Cip1}$). They showed that dominant negative Ras expression or the ERK kinase (MEK1) inhibitor PD98059 reduced phosphorylation of Smad1 by TGFβ stimulation in intestinal epithelial cells, and also inhibited the response of the 3TP-luciferase reporter gene to TGFβ (Yue, J., et al., *Oncogene* 18:2033–7, 1999). More recently, Mulder and Yue have reported the involvement of Ras, MKK4 and MEK1 in the formation of a Fra-2/JunD complex at an Ap-1 site in the TGFβ1 promoter. The Fra-2/JunD complex forms and activates TGFβ1 expression in response to TGFβ3 on intestinal epithelial cells (Yue, J. and K. M. Mulder, *J. Biol. Chem.* 275:30765–73, 2000). The activation of TGFβ1 expression was blocked by dominant negative mutations in Smad3 and Smad4, but the mechanism of this interference was not clear in that Smad3 and Smad4 were not detected in the transcriptional complex at the AP1 site formed in response to TGFβ3 (Yue, J. and K. M. Mulder, supra, 2000). In addition to MAPK involvement in TGFβ responses, PI3-kinase has been implicated in responses to TGFβ through the use of the PI3-kinase inhibitor Iy294002 or expression of dominant negative forms of PI3-kinase in rat hepatocytes. Peron and colleagues propose that EGF potentiates TGFβ signaling in rat hepatocytes by stimulation of AP1 through PI3-kinase and interaction of AP1 with Smad3 (Peron, P., et al., *J. Biol. Chem.* 27:27, 2000).

Up until recently, studies in genetic models systems such as *Drosophila* had emphasized the roles of the Smad-related genes in pathways activated by the TGFβ superfamily ligands such as dpp. However a recent study has found that a p38 MAPK in *Drosophila* (D-p38b) can alter the same phenotypes as dpp during *Drosophila* development. Dominant-negative forms of D-p38b and the p38 inhibitor SB203580 caused dpp-like phenotypes in *Drosophila* wing development and, importantly, suppressed mutant phenotypes caused by overexpression of an activated dpp receptor (Adachi-Yamada, T., et al., *Mol. Cell. Biol.* 19:2322–9, 1999). These results are consistent with D-p38b functioning in a positive response to *Drosophila* dpp signaling, perhaps cooperatively with Mad and Medea, the *Drosophila* Smads.

An example of a Smad-independent mechanism is the recent report that the activated TGFβ receptor directly phosphorylates protein phosphatase2A-Bα. This leads to association of the three PP2A subunits with $p70^{s6k}$, dephosphorylation and inactivation of $p70^{s6k}$, inhibition of translation of specific mRNAs and cell cycle arrest (Petritsch, C., et al., *Genes Dev.* 14:3093–101, 2000). In mammary epithelial cells, this translational mechanism provides a Smad-independent G1 cell cycle arrest in response to TGFβ whereas in other cell lines and in murine embryonic fibroblasts TGF-β does not inhibit $p70^{s6k}$ and Smad signaling is both necessary and sufficient for G1 arrest (Patritsch, C., et al., supra, 2000). This cell-type specificity appears to depend on whether the Bα subunit of PP2A is expressed in the cells.

Oncogenic Ras causes mammary epithelial cells to respond to TGFβ so as to enhance their invasive and metastatic potential instead of being growth inhibited (Oft, M., et al., *Genes Dev.* 10:2462–77, 1996; Oft, M., et al., *Curr. Biol.* 8:1243–52, 1998). Downward and colleagues reported a similar phenomenon in MDCK epithelial cells. Activated Raf increased the secretion of TGFβ, which is growth inhibitory to the parental MDCK cells. Cells with activated Raf were refractory to the growth inhibitory effects of TGFβ but retained TGFβ-dependent invasiveness (Lehmann, K., et al., *Genes Dev.* 14:2610–22, 2000). Raf-expressing cells lost their apoptotic responses to both TGFβ and TNF-α but retained TGF-β induced activation and nuclear translocation of Smad2, 3 and 4. Loss of the apoptotic response occurred more rapidly, within 8–24 hours, whereas loss of all growth inhibitory responses to TGFβ occurred after several weeks of Raf activation, coincident with the epithelial-mesenchymal transition in these cells (Lehmann, K., et al., supra, 2000). Iglesias and colleagues studied the effects of activated Ras on TGFβ signaling in murine keratinocytes (Iglesias, M., et al., *Oncogene* 19:4134–45, 2000). Similar to earlier reports from Mulder and colleagues of rapid activation of Ras and MAPK by TGFβ, Iglesias and colleagues observed maximal levels of Ras-GTP two minutes after TGFβ stimulation and nuclear localization of ERK approximately 30 minutes after TGFβ stimulation. In the Ras transformed keratinocytes, dominant negative Smad4 did not alter the TGFβ induction of $p21^{Cip1}$, but the MEK inhibitor PD098059 did block this response to TGFβ. Furthermore, they reported that the dominant negative Smad4 led to hyper activation of Ras/Erk signaling, increased levels of urokinase secretion and more poorly differentiated carcinomas (Iglesias, M., et al., supra, 2000). Additional evidence for the complex relationship between oncogenic Ras and TGFβ signaling comes from analysis of human prostate cancer cells (Park, B. J., et al, *Cancer Res.* 60:3031–8, 2000). TGFβ stimulates the growth of the prostate cancer cell line TSU-Pr1 but in the presence of PD098059, TGFβ is growth inhibitory. The mitogenic effect of TGFβ was not inhibited by expression of dominant negative Smad2, Smad3 or Smad4 (Park, B. J., et al, supra, 2000). A recent report on the role of TGFβ in the epithelial to mesenchymal transition in tumor progression has identified another interesting pathway. Moses and colleagues report that TGFβ rapidly activates RhoA in a process that is not blocked by dominant-negative Smad3 or Smad7 and that causes induction of stress fibers and mesenchymal characteristics in mammary epithelial cells (Bhowmick, N. A., et al., *Mol. Biol. Cell.* 12:27–36, 2001).

Smad-P Protein—Protein Interactions

As the previous section illustrates, there are likely to be several pathways involved in TGFβ signaling. Some of these, such as the MAPKs and PI3 kinase are clearly also very important in cell responses to factors acting on receptor tyrosine kinases such as EGF, PDGF and the FGFs. There are already chemical inhibitors of some of these pathways and much work still being done to discover new pharmacological inhibitors of these pathways. In contrast, there is as yet, no pharmacological inhibitor specific to the Smad pathway.

BRIEF SUMMARY OF THE INVENTION

In one embodiment, the present invention is a method of screening selective inhibitors or activators of Smad target protein binding. In a preferred embodiment, the method comprises the steps of obtaining a phosphorylated Smad protein or phosphorylated Smad protein complex, allowing the phosphorylated Smad protein or protein complex to interact with a target protein peptide in the presence of a test compound, and analyzing the binding of phosphorylated Smad protein complex or protein and the target protein or peptide, wherein a perturbation of binding indicates that the test compound is an inhibitor or activator of Smad target protein interaction.

In another embodiment, the present invention is a isolated phosphorylated Smad protein or an isolated phosphorylated Smad protein complex.

In another embodiment, the present invention is a method of producing an isolated phosphorylated Smad protein comprising the steps of obtaining a cDNA molecule encoding a Smad protein, cloning the cDNA into a baculovirus expression vector and transfecting Baculovirus cells with the vector, co-infecting the Baculovirus cells with a virus producing a membrane targeted, constitutively activated human TGFβ Type I receptor, and purifying the phosphorylated Smad protein from the baculovirus cell.

It is an object of the present invention to screen for selected inhibitors or activators of Smad target protein binding.

It is another object of the present invention to screen for selective inhibitors or activators of TGFβ signal transduction.

Other objects, features and advantages of the present invention will become apparent after review of the specification, claims and drawings.

DESCRIPTION OF THE SEVERAL VIEWS OF THE DRAWINGS

FIG. 1A is a commasie-stained SDS-PAGE gel of fractions 1–7 from the nickel chelate affinity columns. Total lysates from sf-9 cells infected with baculovirus expressing Smad2 (left side of gel) or baculovirus expressing Smad2 and activated Type I receptor (right side of gel) were applied to the columns.

FIG. 3 is a list of peptides used for HTRF Smad binding Assays.

FIG. 6A: Lane 1. Molecular Weight Stds. (Bio-Rad), Lane 2. Pull down Smad 2P with GST-CBP; Lane 3. Pulldown Smad2-P with GST-trx-FAST aptamer. Lane 4. No Pulldown with an unrelated GST-trx aptamer.

DETAILED DESCRIPTION OF THE INVENTION

A. In General

Figure 1:
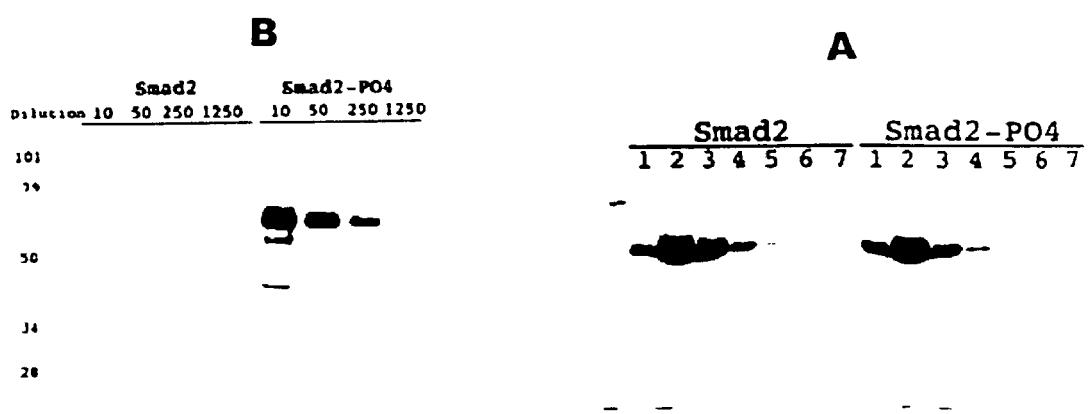
FIGS. 1A and B are copies of stained electrophoretic gels documenting the purification of Smad2 and Phosphorylated Smad2 from sf9 Cultures.
FIG. 1B is a Western blot of four dilutions of the pooled fractions 1–4 probed with an anti-Phospho-Smad2 antibody. Bound antibody was detected by HRP-conjugated secondary, ECL reagent and exposure to X-ray film.

The present invention exploits the hypothesis that inhibition of the transforming growth factor beta (TGFβ) signal transduction pathway by small molecules can provide efficacious and specific intervention in some diseases. TGFβ has been implicated in a broad variety of human diseases including cancer, immunoregulation, wound healing and tissue repair. In cancer, TGFβ facilitates the progression and spread of tumor cells. The tumor-derived TGFβ can aid tumorigenicity by direct actions on the cancer cell, by induction of angiogenesis, by local or systemic immunosuppression, and by alterations of stromal tissue that facilitate invasiveness.

We believe that selective perturbation of TGF-β responses may be achieved by targeting the specific interactions of phosphorylated Smad (Smad-P) complexes with target proteins and peptides and that selective intervention strategies are possible by interfering with a specific sub-set of Smad-P's interactions. One focus of the present invention is to screen for small molecule inhibitors ("test compounds") that can be used to perturb a distinct subset of Smad-P functions for evaluation in biological assays, including cell-based models of disease.

B. Selection of Test Compounds

Test compounds may include small chemical compounds, such as synthetic organic compounds, combinatorial libraries of synthetic or natural products or natural products in crude form or in extracts as well as other possible inhibitors, such as antibodies, peptides and peptide mimetics. Synthetic organic chemical libraries may include, but are not limited to, Molecular Design and Discovery/Timtec's (Ontario) 20,000 compound library Chemiv's (San Diego, Calif.) 220,000 compound "Historical Collection," Nanoxyn's (Tucson, Ariz.) 60,000 compound "Plug and Play" chemical library, Cerep's (France) Odyssey 5000 lead-seeking library, and ChemBridge Corporation's (San Diego, Calif.) DIVER-Set libraries (10,000–50,000 compounds). Natural product libraries may include, but are not limited to, New Chemical Entities (Bothell, Washington) "Premium Library" of microbial fermentation and plant tissue extracts, Drug Discoveries (United Kingdom) Natural Product library of plant extracts, or libraries available from the National Institutes of Health Synthetics Repository and Natural Products Repository.

Inhibitory ligands or "test compounds" can also be RNA aptamers or peptide aptamers. The term aptamer was derived from the Latin 'aptus', to fit (Ellington, A. D. and J. W. Szostak, Nature 346:881–822, 1990). Brent and colleagues have defined peptide aptamers as "proteins that contain a conformationally constrained peptide region of variable sequence displayed from a scaffold" (Geyer, C. R., et al., Proc. Natl. Acad. Sci. USA 96:8567–8572, 1999.

The development of protein scaffolds began with the recognition that immunoglobulins function through the use of a conserved framework region and a spatially defined hypervariable region. Subsequently, several proteins of small size, high stability and ease of production have been tested as protein scaffolds for various applications in basic research and medicine (Skerra, A., J. Mol. Recognit. 13:167–187, 2000. As a tool to disrupt protein—protein interactions in the Smad enhanceosome, peptide aptamers would be suitable. Brent and colleagues have used peptide aptamers to inhibit cyclin-dependent kinase 2 (Colas, P., et al., Nature 380:548–550, 1996. They created a library ($2.9 \times 10^9$) of constrained 20 amino acid random peptides displayed in the active site loop of E. coli thioredoxin. The library was screened against a bait of cdk2 and several aptamers with dissociation constants in the 30–120 nM range were identified. The aptamers blocked cdk2-mediated phosphorylation of histone H1. An important result was that a peptide aptamer could block the interaction of cdk2 with histone H1 but did not inhibit cdk2-mediated phosphorylation of Rb (Cohen, B. A., et al., Proc. Natl. Acad. Sci. USA 95:14272–14277, 1998. In contrast, the cdk2 inhibitor p21 blocks the phosphorylation of both substrates. Binding of the peptide aptamer to cdk2 was reduced only by mutations near the cdk2 active site. Inhibition of the cdk2 phosphorylation of histone H1 was also achieved by the free 20 amino acid peptide, but the $IC_{50}$ was 1000-fold higher than the same peptide displayed on the trx scaffold. Expression of the trx peptide aptamer from a CMV promoter in Saos-2 cells inhibited cell-cycle progression (Cohen, B. A., et al., supra, 1998). In addition to selection of aptamers through specific protein—protein interactions, aptamers have been selected in a phenotypic assay for aptamers that overcame α-factor-induced cell cycle arrest in yeast (Geyer, C. R., et al., supra, 1999). The targets for the aptamers were then identified by using the aptamers as baits in a yeast two-hybrid screen.

Peptide aptamers on the thioredoxin scaffold have also been used to disrupt E2F-DP1 (Fabbrizio, E., et al., Oncogene 18:4357–4363, 1999) and p53-mdm2 interactions (Bottger, A., et al., Curr. Biol. 7:860–869, 1997). Peptide aptamers that bind E2F1 were selected in a yeast two hybrid system using the DNA binding and DP heterodimerization domains of E2F1 as baits. The library was the 20-amino acid peptide displayed in thioredoxin developed by Brent and colleagues (Colas, P., et al., supra, 1996). Six positives were selected from $5 \times 10^5$ bait-prey co-transformants. One of the six had a four amino acid motif (WIGL) that is also present in the DP1 heterodimerization domain. Expression of the WIGL-containing gbaptamers in the Chinese Hamster fibroblast cell line CCL39 caused a decrease in the number and size of colonies when compared to expression of the thioredoxin scaffold alone. A GST-thioredoxin aptamer was injected into hs68 cells and blocked DNA synthesis as measured by BrdU incorporation. The GST-trx-aptamer was much more potent than free peptide in causing a G1 block in cells (Fabbrizio, E., et al., supra, 1999).

Mdm2 is a key regulator of p53 function. Lane and colleagues designed a thioredoxin peptide aptamer by inserting a 12 amino acid Mdm2-binding peptide at the thioredoxin active site (Bottger, A., et al., supra, 1997). Introduction of the peptide aptamer into cells caused an accumulation of p53 protein and activation of p53-responsive reporter genes. These effects were consistent with the trx-aptamer interfering with Mdm2-mediated degradation of p53. Lane and colleagues used an optimized p53 peptide and the wild-type p53 peptide in the trx scaffold. The optimized peptide aptamers had an $IC_{50}$ of 0.3 μM, approximately 50-fold better than the 15 μM $IC_{50}$ of the wild-type p53 aptamer. Mutation of three key amino acids in the peptide to alanine eliminated binding of the peptide aptamers. The optimized peptide aptamers inhibited the p53-Mdm2 interaction with the same strength as full-length p53. The p53 peptide aptamers were expressed in cells under the control of a CMV promoter. The expression construct was microinjected into a rat thyroid epithelial cell line stably transfected with a p53-responsive promoter or was co-transfected into human osteosarcoma cells with p53-responsive reporter plasmids. The peptide aptamers interfered with the Mdm2-p53 interaction, causing elevation of p53 levels and cell cycle arrest (Bottger, A., et al., supra, 1997).

A suitable peptide aptamer for the present invention could be obtained by screening a peptide aptamer library similar to those reported by Brent and colleagues (Colas, et al., supra, 1996) for peptide aptamers that bind to phosphorylated Smad proteins or by insertion of a known Smad interaction motif into an appropriate scaffold molecule that would limit the peptide's conformational degrees of freedom. For example, an oligonucleotide encoding a Smad interaction motif could be inserted by standard molecular biological techniques into the coding region of a gene that encodes a structurally rigid scaffold such as thioredoxin A or GFP. Expression of the resulting fusion gene would generate a protein in which the Smad interaction motif is displayed on a conformationally rigid scaffold, i.e. as a peptide aptamer.

The approach allows facile testing of combinatorial intervention strategies. The proposed screen will provide reagents for perturbing the TGFβ signaling pathway, identify target interactions that are important in specific pathological states, and identify structures of small molecules that are good ligands for Smad-P in the TGFβ pathway.

C. Formation of Phosphorylated Smad Complexes (Smad-P)

In order to perform the method of the present invention, one must first produce suitable Smad-P protein or protein complexes. Smad-P proteins or protein complexes preferably encompass isolated Smad proteins that are in the active conformation induced by phosphorylation of the Smad protein by a receptor kinase. The Smad-P protein may comprise a single phosphorylated Smad protein, e.g., phosphorylated Smad2 or phosphorylated Smad3. The Smad-P complex may contain multiple Smad proteins, one or more being phosphorylated, e.g., phosphorylated Smad2 together with Smad4 is a preferred combination. The exact stoichiometry of the Smad proteins in the complex is not defined and, at the present time, it is uncertain what the stoichiometry is of the native in vivo complex. The present invention contemplates a Smad-P complex that is monomeric or multimeric.

Preferred proteins are Smad proteins phosphorylated on one or more of the three C-terminal serines in Smad2 or Smad 3. This is the site of action of the activated receptor that we use. Smads 1, 5 and 8 are phosphorylated in a similar manner and are another preferred embodiment.

The Examples below describe a preferred isolation method. In brief, we obtained cDNAs from Dr. Massagué (Sloan-Keftering Cancer Center) and cloned the cDNAs into baculovirus or bacterial expression vectors (Table 2 in the Examples). Smad cDNAs have been identified by many different laboratories and are readily available from multiple sources. In addition, the published DNA sequences of the Smad cDNAs enable the recovery of any Smad cDNA using synthetic DNA oligonucleotide primers and the polymerase chain reaction from any isolated or commercially available preparation of total mRNA or cDNA.

Full-length Smad proteins would then preferably be purified from the Sf9 cell lysates. Sf9 cells are from *Spodoptera frugiperda* (fall armyworm) cells, but one could also use other cell lines optimized for expression including the Hi-5 cell line from Invitrogen. (See, for example "Baculovirus Expression Vectors-A Laborabory Manual" DR O'Reilly, L K Miller and V A Luckow, 1994, Oxford University Press).

To produce phosphorylated Smad2 or Smad3, the cells are preferably co-infected with a virus producing a membrane-targeted, constitutively activated human TGFβ Type 1 Receptor (Alk5 T204D). As the Examples disclose, affinity purification on metal-chelete resin yields proteins that are >90% pure.

Smad proteins could also be produced in other expression systems including bacterial, yeast or mammalian cell expression systems. Production of the proteins in bacterial systems may be complicated by insolubility of the recombinant protein in the bacteria and the need for solubilization of these complexes and refolding of the solubilized proteins. Phosphorylation of the Smad proteins to induce the active conformation might be achieved by co-expression of an appropriate kinase activity in the expression system or by the development of an in vitro kinase assay in which the purified recombinant Smad protein would be exposed to a kinase activity that catalyzed phosphorylation of the appropriate amino acids on the Smad protein to induce the active conformation.

Smad2 isolated from the co-infected cells is phosphorylated at the C-terminal serines as detected on Western blots with anti-phospho Smad2 antibody. To produce the Smad2–Smad4 complex, one would preferably infect cells with viruses for both Smad proteins and with virus expressing the activated Type I receptor. The complex can be purified by sequential affinity purification on columns recognizing the his-tag on Smad 2 and the strep-tag on Smad4 (see, for example, FIG. 2 in Examples).

D. Selection of Smad-P Interaction Partner

To perform the assay of the present invention, one must create an interaction between a phosphorylated Smad complex and a specific nuclear transcriptional regulatory factor, which we term a "target protein or peptide." We believe the best candidate for a target that is specific to TGFβ signaling, based on current knowledge, is the interaction of activated Smad-P complexes with a diverse set of nuclear transcriptional regulatory factors listed in Table 1. Table 1 exemplifies a broad variety of target proteins but is not all-inclusive. There are undoubtedly other target proteins that will be found. Table 1 provide a fairly complete list of what is currently known and, more importantly, the diversity of protein types that interact with Smad proteins.

The "target protein or peptide" may not comprise the entire protein or peptide such as those disclosed in Table 1, but may be some portion or fragment of the protein or peptide that comprises the Smad interaction domain. We mean for the term "target protein or peptide" to include use of these portions or fragments.

One with skill in the art could identify other target proteins using well characterized methods for identifying protein—protein interactions. These include, but are not limited to, two-hybrid screens in bacteria, yeast or mammalian cells, in vitro screens of expression libraries in bacteriophage, bacteria, yeast or mammalian cells, and purification of Smad-containing protein complexes from cells and identification of associated proteins in the complex by purification and amino acid sequencing and/or mass spectroscopy. Preferred binding partners could be of two classes. One class which is an extension of Table 1, is natural binding partners, e.g., proteins that are identified as described above. Preferably, a combination of two criteria are used: (1) demonstration of co-immunoprecipitation with Smad protein to demonstrate that the interaction occurs in mammalian cells and (2) demonstration that the binding is direct (as opposed to being mediated by a third factor) using yeast two hybrid, in vitro transcription-translation followed by immunoprecipitation, or a pull-down or solution-based measure of binding using purified Smad and the purified candidate protein. The assay we describe is a good way of testing direct binding if the candidate can be prepared as a purified protein. One would then require saturable binding to purified Smad protein as with any ligand-protein interaction. It would be useful to broaden claim 4 to be a Smad-interaction domain from any protein established as a Smad binding partner by the criteria used to establish the proteins in Table 1 as Smad binding partners (yeast 2 hybrid, GST-pulldown, co-immunoprecipitation) since those methodologies are now well established as ways of recovering Smad binding partners by anyone in the business. The second class of binding partners would be non-natural. These might be peptide or RNA aptamers identified by screening libraries of random aptamers or, for example, random peptide phage display libraries.

All of the proteins in Table 1 could be obtained by one with skill in the art by obtaining cDNA clones from the laboratories in the cited literature or, using public databases of the sequences of the cDNAs, recovery of any cDNA using synthetic DNA oligonucleotide primers and the polymerase chain reaction from any isolated or commercially available preparation of total mRNA or cDNA. The cDNAs would then be cloned into any of several commercial or widely used expression systems, and the recombinant protein purified. In principle, the sequences in the public databases also enable synthesis of the proteins or specific domains of the proteins directly.

Selective perturbation of TGFβ responses will be achieved by understanding the specific interactions of Smad-P complexes with other proteins and that the selective intervention strategies are possible by interfering with a specific sub-set of Smad-P's interactions. It is likely, however, that efficacious, therapeutic inhibition of TGFβ signaling may require a combination of pharmacological agents so as to alter signaling at both the Smads and at another pathway such as a specific MAPK or P13 kinase. The screens we propose here are well suited to identifying compounds that can be used in such combinatorial strategies.

Most of the proteins listed in Table 1 participate with Smad-P in multiprotein complexes bound to specific DNA elements in transcriptional promoters to activate or repress transcription. The general mechanism can be illustrated by one of the best-characterized Smad-P functions, the activation of the *Xenopus* Mix.2 gene in response to TGFβ or activin. A phosphorylated Smad2–Smad4 complex binds to FAST1 at a specific promoter sequence called the activin response element (ARE) (Chen, X., et al., supra, 1997). The DNA binding domain of FAST1 recognizes the ARE. There is a direct protein—protein interaction between Smad2 and FAST1. Massagué and colleagues demonstrated that 6 amino acids in helix2 of the Smad MH2 domain are sufficient to impart FAST1 binding (Chen, Y. G., et al., *Genes Dev.* 12:2144–52, 1998). Smad1(H2) (Smad1 with helix2 region of Smad2) was activated by BMP signaling and associated with FAST1 whereas Smad2(H1) was unable to associate with FAST1 after TGFβ stimulation (Chen, Y. G., et al., supra, 1998). Smad1 and Smad2 have high sequence identity on either side of helix2 but six amino acid differences at helix2. Similar results were independently reported (Lagna, G. and A. Hemmati-Brivanlou, *Dev. Dyn.* 214: 269–77, 1999).

TABLE 1

Multiple Proteins Interact with the Smad-P Complex

| Protein | Smad-interaction Domain | Domain of Smad Mediating Binding | Reference (all incorporated by reference herein) |
|---|---|---|---|
| AML | RDH region and (AA 371–411) | MH2 domain | Pardali, et al., supra, 2000 |
| ATF-2 | Basic leucine zipper | Smad3 or 4 MH1 | Sano, Y., et al., J. Biol. Chem. 274:8949–57, 1999 |
| CBP | AA 1891–2175 to Smad 2 or 3 and AA 1–596 to Smad4 | Smad3 MH2 AA210–342 or Smad2 AA225–467 and Smad4 AA270–322 | Jacknecht, R., et al., supra, 1998; de Caestecker, et al., supra, 2000; Feng, X.H., et al., Genes Dev., 1998; Topper, J.N., et al., Proc. Natl. Acad. Sci. USA, 1998 |
| FAST | AA 470–493 | MH2αhelix2 | Chen, X., et al., supra, 1997 |
| Hoxc-8 | homeodomain (AA 149–209) | Smad1-MH1 AA 101–144 = H1D1 AA 148–191 = H1D2 | Yang, X., et al., supra, 2000 |
| Jun | AA 223–331 | Smad3 MH1 + linker domains | Zhang, Y., et al., supra, 1998; Liberati, N.T., et al., Proc. Natl. Acad. Sci. USA, 1999 |
| Msg-1 | AA 30–60 | Smad4 MH2 AA 302–552 | Shioda, T., et al., Proc. Natl. Acad. Sci. USA, 1998 |
| Mixer/Milk | AA 283–307 | MH2αhelix2 | Germain, S., et al., supra, 2000 |
| SKI/SNO | AA 197–441 to Smad4 AA 241–441 to Smad2 or 3 | Smad2, 3 or 4 MH2 | Luo, R.S., et al., supra, 1999; Akiyoshi, S., et al., J. Biol. Chem. 1999; Sun, Y., et al., Mol. Cell, 1999 |
| SP1 | AA 252–496 AA 424–542 | Smad2, 3 or 4 MH1 and MH2 | Pardali, K., et al., J. Biol. Chem., 2000; Feng, X.H., et al., EMBO J., 2000 |

TABLE 1-continued

Multiple Proteins Interact with the Smad-P Complex

| Protein | Smad-interaction Domain | Domain of Smad Mediating Binding | Reference (all incorporated by reference herein) |
|---|---|---|---|
| TFE3 | ? | ? | Hua, X., et al., supra, 1999 |
| TGIF | AA 138–192 | Smad2 or 3 MH2 | Wotton, D., et al., supra, 1999 |
| Vitamin D Receptor and SRC-1 | VDR E-domain AA115–300 | Smad3-MH1 AA21–146 | Yanagisawa, J., et al., Science, 1999 |

The domain on FAST proteins that mediate the interaction with Smads was identified through the identification of the Mix family paired-like homeodomain transcription factors Mixer and Milk in Xenopus (Germain, S., et al., supra, 2000). Mixer and Milk mediate TGFβ-induced transcription by recruiting Smad2/Smad4 complexes to the distal element of the Xenopus goosecoid promoter. A conserved motif in Mixer and Milk that is necessary and sufficient for their interactions with Smad is conserved in Xenopus FAST1, human FAST1 and mouse FAST2. Mixer and Milk bind to a different regulatory element at the goosecoid promoter than FAST. Although FAST and Mix family proteins are unrelated, a small conserved sequence was identified in the proteins that bind Smad2. The sequence has a conserved PPNK (SEQ ID NO:1) core. Mutation of the conserved prolines to alanines eliminated binding to Smad2. A peptide of 25 amino acids containing the Mixer Smad interaction motif (SIM) inhibited binding of Mixer or FAST1 to Smad2 (Germain, S., et al., supra, 2000).

Any of the proteins listed in Table 1 or other target proteins not in Table 1 could be used in assays that detect binding to SmadP. Priority might be given to proteins that have been shown to exhibit a biological interaction with Smad proteins in vivo by one or more methods including co-immunoprecipitation from TGF-beta activated cells or cooperative activation or repression of a reporter gene after co-expression of Smad genes and the gene encoding the other protein. To set up the binding assay, one would need to be able to detect the target protein or peptide by use of a specific antibody to the target protein, by incorporation of a specific epitope tag into the target protein or by purification of the target protein and covalent labeling with a readily detectable label, e.g., a fluorescent or radioactive label. One might either use the full length target protein in such an assay or a portion of the target protein that is expressed, for example, as a fusion protein. One might also use a specific domain or motif of the target protein by amino acid synthesis of that domain or motif and labeling of the resulting peptide for detection.

Assays of protein—protein interactions between the SmadP and the target protein or target peptide might use any of several methods for detecting protein interactions including, but not limited to, the use of solid phase assay formats in which one protein is bound to a solid surface of a microtiter well, a filter or a bead or the use of solution assays such as fluorescence resonance energy transfer or fluorescence polarization (See Examples).

E. Screens Using Test Samples

Smad Binding Assays Using Homogeneous Time Resolved Fluorescence (HTRF)

To practice the present invention, one must have an assay for measuring the binding of the target protein or peptide ligand with Smad2. We describe in the Examples a preferable solution based assay that demonstrates that we can identify small molecule peptide ligands that interact specifically with the Smad-P protein target. As shown below, the binding activities have micromolar affinities and specificity.

We chose to use HTRF (also called LANCE by Wallac) because it allows for rapid assays of protein—protein interactions without the washing steps required for a solid-phase ELISA-type assay. The procedure takes advantage of fluorescence resonance energy transfer (FRET) between two fluorescent molecules, a donor and acceptor, which are brought within approximately fifty angstroms of each other (Van Der Meer, B. W., et al., New York: VCH. 177p, 1994). The Packard Eu(K) and XL665 pair are reported to have an energy transfer of 50% at 95 angstoms. If the donor fluorophore is bound to one protein and the acceptor to a second protein, binding of the two proteins can bring the fluorophores into proximity such that FRET occurs. The donor and acceptor pairs are chosen such that the excitation wavelength and emission wavelengths for the two fluorophores are different. Excitation of the donor produces emission from the donor but if FRET occurs, some of the donor energy is transferred to the acceptor fluorophore, leading to FRET-dependent emission from the acceptor fluorophore. The time resolved aspect of the assay is obtained by using lanthanide fluorophores, such as caged europium cryptates, that have long (100–800 microsecond) fluorescence emission properties. Any other fluorescent molecules in the sample that are excited will emit light in the first few microseconds after excitation. The use of time-resolved fluorophores avoid false signals due to fluorescent molecules in the sample.

To establish HTRF assays for Smad protein interactions, we have used reagents from Wallac-Perkin Elmer and Packard that include Europium-cryptate coupled to α-His epitope tag antibody, α-GST antibody or Streptavidin. As acceptor fluorophores we have used allophycocyanin (Packard's XL665) coupled to Streptavidin or direct labeling of GST-fusion protein with IC5 (Dojindo). Reagents are mixed in a 50 microliter volume in the wells of a 384 Black non-treated microwell plate (Corning) and HTRF detected in a Wallac Victor V multimode plate reader. The reader detects emission at 615 nm from the Europium chelate donor and at 665 nm from the APC or IC5 acceptor. Background, cross-talk and high FRET wells can be indicated on the plate map to allow the machine to compute a normalized value as a ratio $Rn=(ET/D) D_{max}$ where $ET=A-BI-(C \times D)$.

A—Fluorescence at 665 nm
BI—Blank (buffer only) at 665 nm
D—Fluorescence at 615 nm
C—Cross-talk correction value calculated from wells containing only donor fluorophore
(from "Quench Correction for LANCE TR-FRET" by Perkin-Elmer Wallace)

Table 3 in the Examples indicates all the values obtained by the reader for a simple test of FRET between a Europium-cryptate αGST antibody (Packard) and a GST-CBP protein labeled with IC5 using either N-ethyl-N'-[5-(N-succinimidyloxy carbonyl) pentyl]-3,3,3',3'-tetramethyl-2,2'-indodicarbocyanine chloride (Dojindo) or N-ethyl-N'-[5-(N-(2-maleimidoethyl) piperazinocarbonyl) pentyl]-3,3,3',3'-tetramethyl-2,2'-indodicarbocyanine chloride.

Other assay methods may be equally suitable. Other suitable assay methods should enable the detection of the protein—protein interaction between the SmadP and the target protein and should enable the screening of multiple, preferably thousands, of compounds for potential inhibitors. The pharmaceutical industry has developed several such assay formats. These include but are not limited to ELISA-type assays in which one protein is bound to a solid surface (Microtiter well, filter, bead, glass slide or other) and the binding of the second protein is detected by radioactivity (scintillation proximity assays (SPA)), luminescence, surface plasmon resinance, fluorescence or absorption methods.

Protein—protein interactions can also be detected in solution using fluorescence resonance energy transfer, homogeneous time resolved fluorescence, fluorescence polarization or light scattering. These methods and others are all well-established in the industry.

One would next screen test compounds for their ability to preturb the Smad-P-target protein interaction. The Examples below demonstrate a screen of 98 compounds.

To be useful for screening, an assay format should exhibit certain statistical properties. One statistical parameter that is gaining acceptance in the industry for evaluation and validation of a screening assay is the Z-value. (Reference—J.-H. Zhang, T. D. Y. Chung, and K. R. Oldenburg (1999) A Simple Statistical Parameter for Use in Evaluation and Validation of High Throughput Screening Assays. *J. Biomolecular Screening* 4:67–73.) The Z-value is reflective of both the assay signal dynamic range and the data variation associated with the signal measurements.

$Z=1-[(3\sigma_s+3\sigma_c)/(\mu_s-\mu_c)]$ where $\sigma$ is the standard deviation and $\mu$ the mean of the sample and control data sets.

Assays with Z values above zero can be used for screening compounds. Assays with Z-values abobe 0.5 are considered "excellent assays". In the HTRF assay format described here, Z-values have been calculated using three different concentrations of peptide inhibitor at four different times. 10 uM inhibitor gave ~50% inhibition of binding to Smad2P.

| Concentration of Inhibitor | Z values | Z values | Z values | Z values |
|---|---|---|---|---|
| 10 uM | 0.564 | 0.567 | 0.787 | 0.479 |
| 20 uM | 0.670 | 0.661 | 0.823 | 0.711 |
| 50 uM | 0.831 | 0.879 | 0.920 | 0.828 |

Compounds that provide 50% or greater inhibition of binding would be easily detected in the Smad2P binding assays. In this data set, inhibition of the control Smad binding by 15% would have provided a Z-value close to zero. The Z-value calculation indicates that the assay could detect active compounds that provided >15% inhibition of control binding. The exact limit would be determined empirically and would depend on the assay format and any improvements or reductions in well-to-well variability. We contemplate that some compounds could increase binding of the protein target to Smad2P, e.g. by causing a conformational change in Smad2P that causes it to have better binding for the protein target. The assays would be equally sensitive to detecting these activators or facilitators of binding.

To define the ability of the assay to detect compounds, one can use peptide inhibitors of the same amino acid sequence as the peptide ligand or representing motifs of the protein targets.

F. Effects of Ligands on TGFβ Signal Transduction Components

One may wish to characterize the selectivity of the active compounds identified in the screens for the TGFβ pathway and the molecular mechanisms responsible for their effects in cell-based assays. As discussed above, there are a growing number of reports of non-Smad signal transduction events in response to TGFβ. These include MEKK1, PP2a and Rho. Published assays that detect activation of MEKK1, PP2a and Rho will be used to determine any interference or activation of these components in the presence of TGFβ and the Smad inhibitors.

(i) Effect of Ligands on TGFβ Responses in Cell Based Assays

Active compounds that have been selected for their potency and specificity will preferably be tested on human keratinocyte cell cultures. We are using a new human keratinocyte cell line called NIKS because it exhibits very normal behavior in culture, exhibits no transformed phenotypes, and is very sensitive to TGFβ (Allen-Hoffmann, B. L., et al., *J. Invest. Dermatol.* 114:444–55, 2000). We also use other cell lines commonly used to study TGFβ including human HaCaT keratinocytes, HepG2 liver carcinoma cells, and mink lung epithelial cells. One might use these cell lines or other suitable lines. Suitable lines include any cell line with a measurable response to TGF-beta family ligands including responses such as proliferation, apoptosis, migration, changes in subcellular localization of specific proteins, changes in the phosphorylation state of specific proteins, changes in the level of specific proteins, increases in specific gene expression or decreases in specific gene expression. One would typically carry out dose-response titrations on active compounds to test for cell toxicity using, for example, the Promega CellTiter 96 and CytoTox96 assays. One would also test for induction of apoptosis in the cells by the compounds, for example by using the Promega DeadEnd Apoptosis detection kit.

To test for effects on TGFβ signal transduction in human cells, one might assay the TGFβ inhibition of BrdU incorporation that is caused by the TGFβ-induced G1 arrest of the cells. Dose-response titrations of non-cytotoxic levels of the compounds will be run to test for interference with the TGFβ cell cycle arrest; this will be detected by an increase in BrdU incorporation. One would also examine TGFβ induction of PAI-1, Smad7 and SnoN in the cells. These three genes all give a rapid (1 hour) increase in mRNA in response to TGFβ. To determine this, we have carried out preliminary analysis of the transcriptional responses to TGFβ in the NIKS human keratinocyte cell line using the GEM array service of Incyte. This preliminary study revealed several known responses to TGFβ after 1 hour including induction of PAI-1, SNO, and Smad7 expression.

To test the effects of the compounds on mRNA levels one would typically perform Northern blots or real-time PCR using the ABI7700 available in the McArdle Macromolecular Analysis Facility. For some of the transcriptional interactions, e.g., with FAST1, we do not know what the endogenous targets are in human cells at this time. To test whether a compound or peptide can interfere with Smad-P/FAST1 in intact human cells, one would use the ARE-luciferase reporter gene co-transfected with a FAST1 expression construct. Several labs have used this assay to study Smad-P/FAST1 dependent transcription. Additional candidate gene expression responses will be tested to determine whether a compound or peptide interferes with TGFβ induction. For example, one would measure induction of fibronectin and collagen genes in response to TGFβ, as these are key genes in TGFβ-induced fibrosis.

As discussed above, there are several non-Smad pathways that are activated by TGFβ. Several of these can be modulated by chemical inhibitors such as the MEK inhibitor PD98059, the p38 inhibitor SB203580 and the PI3 kinase inhibitor Ly294002. In all of the cell based assays of TGFβ effects on cell proliferation, gene expression or cell invasiveness, one would typically compare the effects of the Smad inhibitors to the effects of the inhibitors of non-Smad signaling on the assay endpoint.

One might be interested in determining whether a combination of a Smad inhibitor and one of these other inhibitors will have synergistic effects on cell responses to TGFβ, such that a subthreshold dose of each inhibitor is effective when used in combination. This would provide the first clue as to how to achieve greater pharmacological specificity in modulating TGFβ responses.

(ii) Determine Effects of Smad-Inhibitory Ligands on Other Signal Transduction Pathways It may be important to determine whether active compounds have pleiotropic effects on other signaling pathways. To evaluate this, one would preferably use a series of pathway-specific reporter genes. One might test for effects on the NF-κB, CRE, Ap-1, SRE, SRF and p53-mediated transcriptional activation using the PathDetect kits from Stratagene. These provide a readily measurable luciferase reporter gene driven by a pathway-specific synthetic enhancer element that is activated by co-transfection with an expression plasmid encoding an active, upstream, pathway activator, e.g., MEKK or PKA. One might examine the selectivity of the active compounds for effects on BMP signaling using a BMP-responsive reporter gene generated by Miyazono and colleagues with a portion of the Smad-6 promoter (Ishida, W., et al., *J. Biol. Chem.* 275:6075–9, 2000). Compounds that affect other pathways will be more likely to have toxicity or side-effects in the animal models. Because several of the gene reporter assays use artificial promoters and overexpression of upstream pathway components, they may not be sensitive enough to detect interference by some compounds. These assays will, however, provide a rapid first screen for nonselective effects. Once a few compounds are chosen by the results of biological assays, it may be important to examine endogenous gene expression responses or cellular phenotypes in response to other cytokines or growth factors to more rigorously determine the selectivity for the TGFβ pathway.

(iii) Cell-Based Assays of Invasiveness

One may wish to characterize the active compounds on TGFβ-induced invasiveness. CT26 cells (from a chemically-induced murine colon carcinoma) exhibit TGFβ-dependent invasive behavior in a 3-D collagen gel assay (Oft, M., et al., supra, 1996). One may wish to also examine other human cell lines that have been previously shown to exhibit TGFβ-dependent invasiveness (nasopharyngeal carcinoma KB, kidney carcinoma MZ-1795 and mammary carcinoma T47D) in collagen gel in vitro assays (Oft, M., et al., supra, 1996; Oft, M., et al., supra, 1998). The 4T1 mammary carcinoma cell line has been used to demonstrate a TGF-β dependent invasiveness (McEarchern, J. A., et al., *Int. J. Cancer* 91:76–82, 2001). Basal levels of cell migration but minimal invasive properties were observed in the absence of TGF-β1. McEarchern used 12-well transwells (Corning) to quantify migration through untreated transwells or invasion through collagen treated transwells. Smad inhibitory active compounds will be assayed for their ability to inhibit the TGFβ effects in these cellular assays. One would preferably establish the dose-response behavior of each compound to determine the relative potencies and compare the effects of the Smad inhibitors in these assays to inhibitors of non-Smad signaling components activated by TGFβ, such as PD98059, SB203580, and Ly294002.

G. Characterization of Cell-Permeable Peptides and Non-Peptide Ligands in Animal Models in which TGFβ is Implicated in the Disease Etiology or Progression.

One would preferably focus on three models: To test the in vivo efficacy of molecules that perturb TGFβ signal transduction: tumor invasiveness, bleomycin-induced lung fibrosis, and chronic rejection of a rat infrarenal aortic allograft. These models were chosen because previous studies using anti-sense, dominant-negative constructs or neutralizing antibodies have all established a causal role for TGFβ in these models and because the models examine three different pathological roles associated with TGFβ: progression of advanced cancers, fibrosis, and inflammation-immune response. Even cell-permeable peptides will be tested in these models. The 11 amino acid protein transduction domain from HIV TAT protein has been used to get bioactive peptides into cells in animal models. Intraperitoneal injection of a fluorescently labeled peptide led to uptake of the peptide by blood cells, the brain, and skeletal muscle. Injection of TAT-βgal (116 kd) produced uptake in liver, kidney, lung tissue, and brain.

Administration of the test compound in all three models may be guided by previous studies of related molecules. If we have ligands that interfere with different Smad-P functions we will evaluate combinations of ligands in the animal models to determine whether this strategy will allow for greater efficacy and reduced side-effects. A natural product compound could be provided by oral gavage (used with cyclosporin and mycophenolate mofetil in), or by intraperitoneal injection (used with pifithrin-a 2.2 mg/kg). Cell permeable peptides have also been administered by intraperitoneal injection and shown biological activity in animal models (1.5 mg/injection). Furthermore, injection of a mouse with 1 mg of a cell-permeable fusion protein every day for fourteen days produced no signs of neurological damage or systemic distress. Another mode of systemic administration that we will try is infusion by a subcutaneous osmotic minipump (Model 2001; Alza Corp., Palo Alto, Calif.) as used by Nakao and colleagues. If systemic administration is observed to be detrimental to the animals, we will try local injection of the compounds at the site of the primary tumor. Preferably, six animals per treatment group would be used as this has provided statistical significance in the models we are using.

The role of TGFβ in tumor invasion may be a key target. Late-stage human tumors overexpress TGFβ that can promote angiogenesis and immunosuppression, suggesting that tumors produce TGFb to benefit the tumor. TGFb promotes progression of skin cell carcinomas from the squamous to more aggressive spindle stage. In addition to affecting the local environment, tumor-dreived TGFβ can have autocrine effects on the tumor cells. For example, TGFβ1 is not expressed in normal liver, but some hepatocellular carcinomas express TGFβ. Although TGFβ is a negative growth regulator of normal hepatocytes, the carcinomas cell proliferation is increased by TGFβ. The tumor cells show aberrant responses to TGFβ including suppression of p15$^{INK4B}$, Smad6, and Smad7 but high levels of PAI-1.

Oft and colleagues have used H-Ras expressing mammary epithelial cells to demonstrate a requirement for TGFβ for the invasive, mesenchymal, spindle cell phenotype. Tumor cell autonomous action of TGFβ is required for invasion and metastasis of the epithelial tumor cells. Oft and colleagues used expression of a dominant-negative TGFβ Type II receptor to demonstrate that several tumor cell lines, including metastatic mouse colon carcinoma and human hnPCC, required the autonomous TGFβ signaling for invasiveness. Following the published procedures used for this model, one may assay for effects of compounds or cell-permeable peptides on EpRas cells and CT26 cells. Tumor cells (1×10$^6$) will be injected subcutaneously into nude mice or syngeneic Balb/c mice. Animals will be evaluated for the size of the tumor every three days. EpRas or CT26 primary tumors will be surgically removed at four weeks or at a size of 2 cm$^3$. Tumor growth will be assessed by weighing the tumors. Tumors will be re-cultured to assay for the mesenchymal cell phenotype caused by TGFβ signaling versus the polarized epithelial phenotype apparent when TGFβ signal transduction is impaired. Mesenchymal phenotypes will be confirmed by morphology in phase contrast microscopy and by immunohistochemical staining for the epithelial molecular markers E-cadherin and Z0.1. In previous reports CT26 cells caused lethal lung metastases three weeks after excision of the primary tumor; cells with impaired TGFβ signaling yielded no lung metastases in 9 months. Evasion of metastatic cells from blood vessels will be measured after intravenous injection of C26 cells in Balb/C mice. Lung metastases should be scorable in 2–4 weeks.

One of the best validated models of TGFβ pathology is bleomycin-induced lung fibrosis. Recent studies have confirmed the role of TGFβ in this model in mice mutant for integrin b6 that fail to activate latent TGFβ1 and mice treated with a Smad7-expressing adenovirus. In the latter study a human type 5 adenovirus vector was used to overexpress Smad7 in the lungs. Following the procedures of Nakao and colleagues, lung fibrosis will be caused by infusion of bleomycin (100 mg/kg) for seven days in 8- to 10-week-old C57BL/6 mice. Infusion will be accomplished by a subcutaneous osmotic minipump (Model 2001; Alza Corp., Palo Alto, Calif.). In addition to the methods of compound administration described above, in this model we will also attempt administration of cell-permeable peptides or compounds by intratracheal injection. Mice will be sacrificed after 4 weeks and lungs fixed in 10% formalin for histology. Hematoxylin/eosin/safran stained sections will be examined for fibrotic foci. Additional tests will include RNA isolation and quantitation of Type I procollagen and TGFβ1 mRNAs using real-time PCR in a ABI 7700 in the McArdle Laboratory Macromolecular Analysis Core Facility; quantitation of collagen content by measuring total hydroxyproline by HPLC, and measurement of leukocyte infiltration into bronchoalveolar lavage fluid. All of these indicators are increased by the bleomycin-induced lung fibrosis.

One might test compounds in the rat aortic model of chronic rejection. Hulleft and colleagues have used this model over the past several years to study the effect of immunosuppressive compounds on intimal hyperplasia associated with chronic rejection. Recently, they have established a key role for TGFβ in this model using adenovirus vectors expressing sense or anti-sense TGFβ message (D. Hullett, personal communication).

Chronic rejection is believed to be caused by immunological injury to the organ mediated by a sustained T-cell infiltrate. Hulleft and colleagues have reported infiltration of CD3$^+$ T cells, monocytes, and macrophages into the graft within 2 weeks after transplant. By four weeks, CD4$^+$, CD8$^+$, and IL2R$^+$ cells were detected. After six months, CD4$^+$ and IL2R$^+$ cells were still present in the neointima of the graft. The model exhibits a dependence of chronic rejection on acute rejection that correlates well with clinical studies. Chronic rejection leads to fibrosis that blocks hollow structures within the tissue, e.g., concentric intimal hyperplasia of blood vessels.

In one example, rats could be anesthetized with ketamine and xylazine to harvest donor abdominal aorta, a 1-cm segment excised just above the aortic bifurcation. The graft could be flushed and placed in chilled saline. The recipient rat would be anesthetized, the native infrarenal aorta removed, and the graft sutured in the orthotopic position, end to end. Total time from removal of the donor graft to placement in the recipient would be approximately 45 minutes. Grafts from ACI rats would be transplanted into Lewis rats. For syngeneic transplants, Lewis rats would be used as both donor and recipient. Six animals per treatment group would be sufficient to obtain statistical significance by a two-tailed student's T test in experiments testing either oral administration of cyclosporin, vitamin D, or mycophenolate mofetil or adenoviral infection of the graft with virus expressing antisense TGFβ. Treated animals would be sacrificed at 3 months.

The grafts will be analyzed after fixation in 10% formalin, embedding in paraffin and generation of 6 micron sections stained with hematoxylin and eosin. Cross-sectional areas could be quantified by computer image analysis. Three readings will be made on each graft to obtain an average area. Percent intimal and medial values could be obtained by dividing intimal or medial area by the area within the external perimeter. In one study intimal area in syngenic grafts was 3509±4325 pixels versus 240,896±87,042 pixels in allogenic grafts at 12 weeks after transplant. Hullett and colleagues have also noted changes in the vascular smooth muscle cells in the model. They observed strong positive staining for β-actin expressing cells in the neointima of the allografts. This is in contrast to the expression of α-actin in normal adult smooth muscle. β-actin expression is a marker for fetal muscle cells that express cytokines and growth factors.

EXAMPLES

Protein—Protein Binding Assays

To produce purified proteins for Smad binding assays, my laboratory obtained cDNAs from Dr. Massagué (Sloan-Kettering Cancer Center) and cloned the cDNAs into baculovirus or bacterial expression vectors (Table 2). Full-length Smad proteins are purified from Sf9 cell lysates.

To produce phosphorylated Smad2 or Smad3, cells are co-infected with a virus producing a membrane-targeted, constitutively activated human TGFβ Type 1 Receptor (Alk5 T204D). Affinity purification on meta1-chelete resin yields proteins that are >90% pure (FIG. 1).

Figure 2:
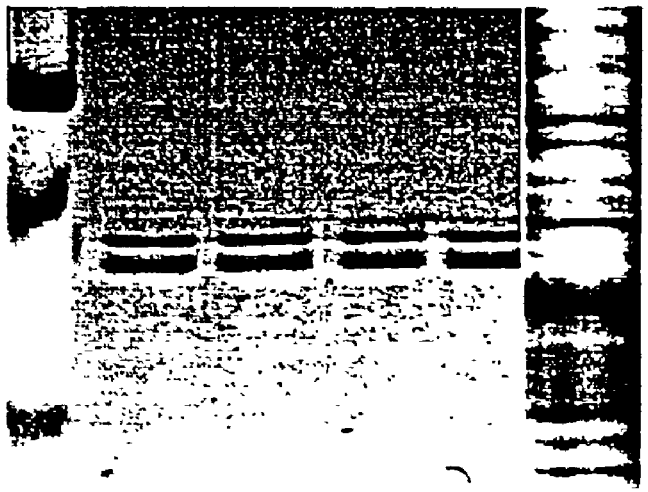
FIGS. 2A and B is a copy of Western blot demonstrating isolation of Smad2–Smad4 complexes from sf9 Cells. Sf9 cells were infected with three baculovirus stocks expressing Smad2, Smad4 and activated Type I receptor. Total lysates were purified on a nickel chelate affinity column to affinity purify his-tagged Smad2 proteins. Fractions containing Smad2 were pooled and applied to a Streptactin column to purify Strep-tagged Smad4 proteins. Fractions were eluted with desthiobiotin. Commasie-stained gels indicated equal intensity bands at positions consistent with the size of Smad2 and Smad4. Probing a Western blot with both anti-Smad2 and anti-Smad4 antibodies detected both bands. Probing the Western with anti-phospho-Smad2 antibody detected only the faster migrating band.
Figure 2:

Smad2 isolated from co-infected cells is phosphorylated at the C-terminal serines as detected on Western blots with anti-phospho Smad2 antibody (Upstate Biotechnology) (FIG. 1). To produce the Smad2–Smad4 complex, we infected cells with viruses for both Smad proteins and with virus expressing the activated Type I receptor. The complex was purified by sequential affinity purification on columns recognizing the his-tag on Smad 2 and the strep-tag on Smad4 (FIG. 2).

TABLE 2

Completed Constructs for Expression and Purification of Smads and Interacting Proteins

| Gene | Amino Acid Sequence Cloned into Expression Vector | Expression Vector | Epitope Tag or Fusion Protein | Yield |
|---|---|---|---|---|
| CBP | 1892–1995 | PGEX-2T | GST-fusion | ~1 mg/ml |
| SARA | 665–721 | PGEX-2T | GST-fusion | 2–3 mg/ml |
| FAST | 221–365 | PGEX-2T | GST-fusion | ~0.5 mg/ml |
| Smad1 | 1–465 | pBlueBac | His | 5 mg/ml |
| Smad2 | 1–467 | pBlueBac | His | 5 mg/ml |
| Smad2 (H1) | 1–467 | pBlueBac | His | N.D. |
| Smad3 | 1–425 | pBlueBac | His | N.D. |
| Smad4 | 1–552 | pBlueBac | Strep | N.D. |
| Alk5 (T204D) | 148–504 | pBlueBac | None | N.D. |
| TGIF | 1–272 | pBlueBac | His | N.D. |
| ATF2 | 1–506 | pBlueBac | His | N.D. |
| SP1 | 1–696 | PGEX-1ZT | GST-fusion | N.D. |
| SP1 | 250–496 | PGex | GST-fusion | |
| SP1 | 421–496 | pGex | GST-fusion | |

Smad Binding Assays Using Homogeneous Time Resolved Fluorescence (HTRF)

As described above, we have developed solution-based assays for measuring the binding of protein and peptide ligands to Smad-P. These assays demonstrate that we can identify small molecule peptide ligands that interact specifically with the Smad-P protein target. As shown below, the binding activities have micromolar affinities and specificity.

Table 3 indicates all the values obtained by the reader for a simple test of FRET between a Europium-cryptate αGST antibody (Packard) and a GST-CBP protein labeled with IC5 using either N-ethyl-N'-[5-(N-succinimidyloxy carbonyl) pentyl]-3,3,3',3'-tetramethyl-2,2'-indodicarbocyanine chloride (Dojindo) or N-ethyl-N'-[5-(N-(2-maleimidoethyl) piperazinocarbonyl) pentyl]-3,3,3',3'-tetramethyl-2,2'-indodicarbocyanine chloride. In Table 3, wells shown include the blank (B03), crosstalk-donor alone (B04), acceptor alone (B05 and B06) and the α-GST-Eu donor plus IC5-GST-CBP acceptor together (B07, B08). Only the last two wells show substantial emission at 665 nm due to FRET between the αGST-Eu bound to the IC5-GST-CBP.

TABLE 3

HTRF between Eu-Anti-GST and IC5-labelled GST-CBP

| Well | Type | Emission 615 | Emission 665 | Normalized Counts |
|---|---|---|---|---|
| B03 | Blank | 351 | 109 | −234 |
| B04 | Crossover (Eu-Anti-GST) | 9582 | 325 | 0 |
| B05 | GST-CBP-IC5 | 373 | 118 | 16 |
| B06 | GST-CBP-IC5 | 346 | 126 | 277 |
| B07 | GST-CBP-IC5 + Eu-Anti-GST | 7486 | 5174 | 6802 |
| B08 | GST-CBP-IC5 + Eu-Anti-GST | 10400 | 9450 | 9107 |

Over the past several months we have developed three HTRF assays for Smad binding interactions. All three assays use a Eu-chelate α-His epitope tag antibody as the donor. The antibody recognizes the hexahistidine epitope tag on the Smad proteins produced in the baculovirus expression system described above. As acceptors, we have used Streptavidin conjugated to allophycocyanin (Packard) that binds to biotinylated peptides. The peptides are synthesized to comprise the Smad interaction domain motif from human FAST or c-Jun (FIG. 3). The FAST 24-mer amino acid sequence is based on the homology between FAST, Mixer and Milk reported by Germain and colleagues (Germain, S., et al., supra, 2000). The 24-mer C-JUN sequence is based on studies using deletions and gene fragments to define the Smad interaction motif (Zhang, Y., et al., supra, 1998; Liberati, N. T. et al., Proc. Natl. Acad. Sci. USA 96:4844–9, 1999). We also have developed an HTRF assay using IC5-GST-CBP, a fusion protein comprising the Smad interaction domain motif from CBP (a generous gift of Dr. Yigong Shi, Princeton University).

The assays are done in a 50 μl volume in the well of a 384-well plate. The assay buffer, as recommended by Packard for their HTRF reagents is 50 mM K-Hepes pH 7.0, 400 mM KF and 0.1% BSA. The high concentration of KF is recommended for the Eu(K) reagents from Packard. By empirical titrations of other components we have found that 1 mM DTT improves our assay results. We have also optimized through many titrations the amount of Smad protein (220 ng/well, ~4 pmoles per well of monomer), the concentration of biotinylated peptide (1 uMolar for FAST and C-JUN), the amount of Eu-anti-His tag antibody (36 ng/well) and the amount of Streptactin-APC (0.5 μg/well). The optimal amounts of the last two reagents were found to be very similar to those recommended by the manufacturer.

Figure 4:
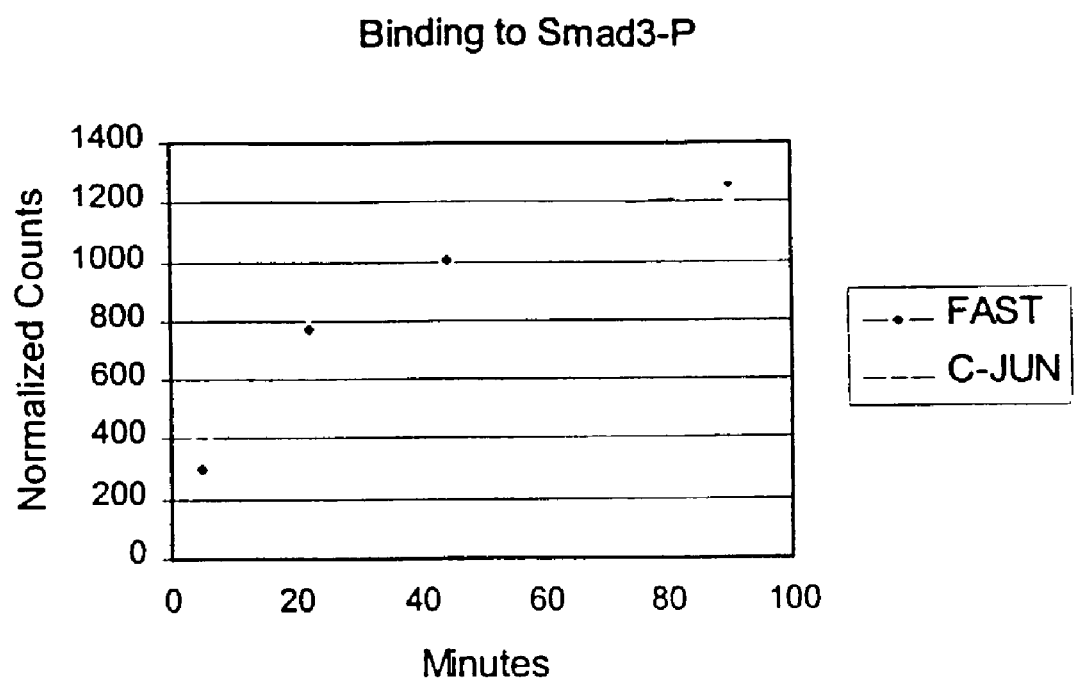
FIG. 4 is a graph of a time course of FAST and Jun peptides binding to Smad3-P.

FIG. 4 demonstrates the time course of binding of 1 μM biotinylated FAST or C-JUN peptides. The binding reaction appears to reach an equilibrium in about 90 minutes. Table 4 shows data to characterize the specificity of the Biotin-FAST binding to Smad-2P. The binding is inhibited by the hFAST-24mer but not by the same peptide in which two prolines have been changed to alanines (hFAST-24mer PP>AA). This is the same mutation that was used in the context of FAST proteins to demonstrate the requirement for these prolines for binding to Smad in cells (Tsukazaki, T., et al., supra, 1998) and serves as a key control for our in vitro binding assays. Although Germain and colleagues focus on the conserved PPNK (SEQ ID NO:1) motif as being a key part of the binding domain, it is not sufficient as shown by the inability of the hFAST-13mer peptide to compete in our assay (Table 4). Additional results supporting the specificity of binding are the inability of cJUN-24mer peptide (Table 4) or CBP-23mer peptide (data not shown) to compete for binding with Biotin-FAST. The inability of these other peptides to compete is consistent with the hypothesis that these Smad ligands bind to distinct sites on the protein complex.

TABLE 4

Specific Inhibition of Biotin-FAST Binding to Smad2-P

| Sample | Average Normalized Counts | Standard Deviation | Percent of Control (minus Background) |
|---|---|---|---|
| Background | 260 | 5 | |
| No inhibitor | 1884 | 42 | 100% |
| 20 μM hFAST 24 mer | 1546 | 70 | 79% |
| 50 μM hFAST 24 mer | 1193 | 56 | 57% |
| 20 μM hFAST PP > AA 24 mer | 1924 | 37 | 102% |
| 50 μM hFAST PP > AA 24 mer | 1865 | 1 | 99% |

TABLE 4-continued

Specific Inhibition of Biotin-FAST Binding to Smad2-P

| Sample | Average Normalized Counts | Standard Deviation | Percent of Control (minus Background) |
|---|---|---|---|
| 20 µM hFAST 13 mer | 2022 | 98 | 108% |
| 50 µM hFAST 13 mer | 1978 | 6 | 106% |
| 20 µM JUN 24 mer | 1984 | 32 | 106% |
| 40 µM JUN 24 mer | 1964 | 66 | 105% |

Table 5 contains data from using the GST-CBP fusion protein that is covalently coupled to the IC5 fluorophore acceptor through the cysteines in the GST portion of the fusion protein. There is no biotinylated peptide or Streptavidin-APC in these assays. Although the counts are lower than we have seen using the FAST or C-JUN peptides, the data show the reproducibility of the FRET counts caused by binding of GST-CBP to Smads in duplicate wells. Other IC-5 labeled GST fusion proteins that we have used do not show any FRET counts above background (data not shown). The lower FRET counts could be due to larger distances between the donor and acceptor molecules in the complex. This might be overcome by using direct labeling of the Smad-P complex with Eu-cryptates rather than the Eu-labeled anti-His tag antibody.

Most importantly, the data reveal preferential binding of GST-CBP to phosphorylated Smad2 and Smad3 and no significant binding to unphosphorylated Smad2 or to Smad4. We have observed similar specificity for pohsphorylated Smad2 and 3 by the biotinylated FAST and C-JUN peptides. The binding of GST-CBP to phosphorylated Smad2 is reversible as shown by the reduction in counts when unlabelled GST-CBP is added after the IC5-GST-CBP binding had reached equilibrium (Table 5, Well D06 and D10). We have also demonstrated that a CBP 23mer peptide (shown in FIG. 3) can compete for binding with the GST-CBP fusion protein (Table 6). The inhibition required fairly high concentrations of peptide, 100 µM for 50% inhibition, but the hFAST 24-mer peptide at 100 µM had no effect on GST-CBP binding (Table 6).

Figure 5:
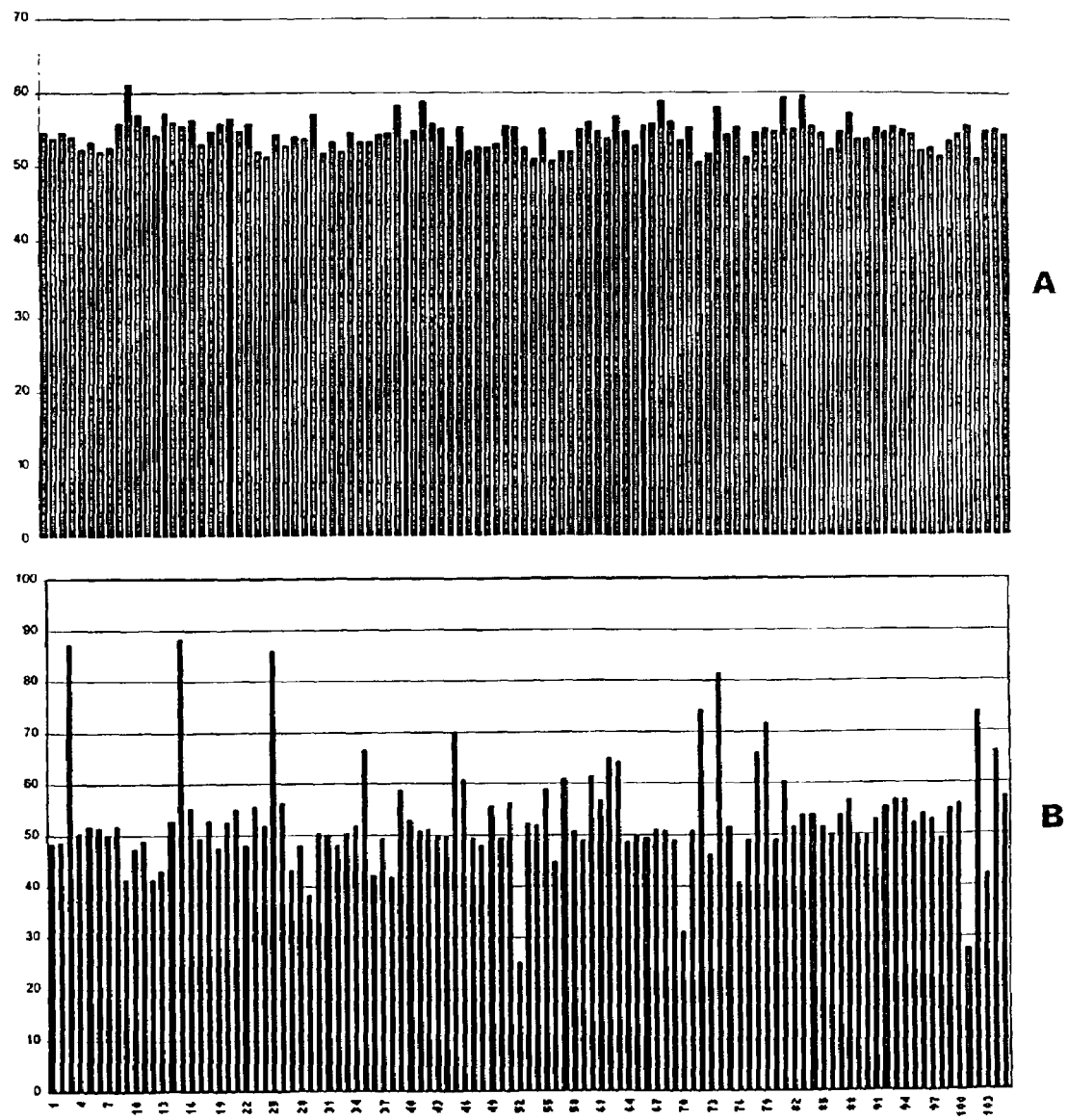
FIGS. 5A and B are bar graphs illustrating a pilot screen of 98 natural product extracts for inhibition of biotin-FAST peptide binding to Smad2P.

To determine whether the HTRF assay formats could be used to screen unknown compounds, I have used a small collection of 98 natural product extracts (FIG. 5). The preliminary results suggest that some extracts provided inhibition of the biotin-FAST to Smad binding. Importantly, several of the extracts with known cytotosic properties had no effect in the assay. The one extract that gave reproducible inhibition in the HTRF assays has no cytotoxic effects on whole cells (G. Marriot, personal communication).

TABLE 5

IC5-GST-CBP Binds Preferentially to Phosphorylated Smad2 and Phosphorylated Smad3

| Well Additions | Normalized Counts |
|---|---|
| D08 No Smad | 260 |
| D05 Smad2P | 593 |
| D06 Smad2P + GST-CBP Competitor | 322 |
| D09 Smad2P | 617 |
| D10 Smad2P + GST-CBP Competitor | 353 |
| D11 Smad2 | 334 |
| D12 Smad2 | 315 |
| D13 Smad2 | 311 |

TABLE 5-continued

IC5-GST-CBP Binds Preferentially to Phosphorylated Smad2 and Phosphorylated Smad3

| Well Additions | Normalized Counts |
|---|---|
| D14 Smad2 | 327 |
| D15 Smad3P | 665 |
| D16 Smad3P | 683 |
| D17 Smad4 | 149 |
| D18 Smad4 | 206 |
| D19 Smad4 | 252 |
| D20 Smad4 | 150 |

TABLE 6

Inhibition of IC5-GST-CBP Binding to Smad2-P

| Sample | Average Normalized Counts | Standard Deviation | Percent of Control (minus background) |
|---|---|---|---|
| Background | 197 | 9 | |
| No inhibitor | 751 | 26 | 100% |
| 50 µM CBP | 587 | 13 | 70% |
| 100 µM CBP | 478 | 89 | 51% |
| 100 µM FAST 24 mer | 743 | 46 | 99% |

A small scale pilot screen of the HTRF assay was used to screen 98 natural product extracts for their effect on biotin-FAST peptide binding to Smad-2P. The samples were methanol and ethyl acetate extracts of sponges collected off the coast of Japan and were generously provided by Professor Gerhard Marriot (UW, Department of Physiology). 100 wells of assay mix were set up and read for HTRF. Very little variability was detected between wells (FIG. 5A). Then 1 ul aliquots of methanol extracts added. The inverse of the normalized HTRF counts are shown in FIG. 5B. An increase in peak height represents inhibition of binding. There were four peaks above 80 in the initial screen, representing an inhibition of almost 50%. On further retesting at lower dilutions, only one of these extracts was active.

Solid Phase ELISA-Type Assay

Activated, Smad-P complexes bind to CBP through interactions with both the Smad2/3 and Smad4 proteins. We tested whether purified Smad-P complexes would have better binding of CBP than unphosphorylated Smad2 and observed that phosphorylation of the Smad protein alters the protein binding to Gst-CBP (Table 7). Smad-P complexes bound >30-fold more CBP than an equivalent amount of unphosphorylated Smad (Table 7). The availability of milligram quantities of purified Smad and Smad-P complex is an important tool for the proposed studies that will establish binding assays for other known Smad binding partners, such as FAST, ATF2, Ski, SP1, TGIF and Vitamin D Receptor.

Table 7, below, tabulates the results of a 96 well Microplate Format Binding Assay of CBP to Smad2 and Phosphorylated Smad2/4 Complex. Duplicate wells are shown with indicated amounts of Smad protein bound per well. Three different dilutions of biotinylated GST-CBP protein were added per well and incubated at room temperture for 1 hour. Wells were washed 3× with TBS+1% tween and Alkaline phosphatase conjugated strepavidin (Tropix) added. Bound conjugate was detected by addition of the CSPD substrate (Tropix) and relative light units (RLU) measured in a Tropix 717 microplate reader at a read time of 1 second per well.

TABLE 7

| GST-CBP Dilution | No Smad | Smad2 0.25 ug/well | Smad2 0.50 ug/well | Smad2P4 0.125 ug/well | Smad2P4 0.25 ug/well | Smad2P4 0.50 ug/well |
|---|---|---|---|---|---|---|
| 1:500 | 4071 | 11125 | 26646 | 72016 | 204232 | 357808 |
|  | 9814 | 8899 | 26315 | 74305 | 190599 | 235669 |
| 1:1000 | 3824 | 6683 | 23041 | 82893 | 181199 | 305821 |
|  | 4043 | 7831 | 23515 | 82282 | 182146 | 322719 |
| 1:2000 | 4086 | 6603 | 11251 | 82190 | 175572 | 302984 |
|  | 3914 | 4344 | 10956 | 85126 | 162063 | 284937 |

Generation of SIM Peptide Aptamers

We chose the thioredoxin (trx) protein scaffold based on the successful studies using trx peptide aptamers to disrupt protein—protein interaction involving cdks, p53 and E2F1 (Colas, P., et al., supra, 1996; Fabbrizio, E., et al., supra, 1999; Bottger, A., et al., supra, 1997). A vector containing the trx gene was purchased from Invitrogen but it contained a large polylinker sequence at the trx active site. We replaced this 60 bp region by PCR mutagenesis with a single RsrII site using the four primers listed in Table 8.

from Table 3. Colonies with the SIM DNA insert were further characterized by restriction digestion and finally by DNA sequence analysis through the entire trx-SIM-trx portion of the plasmids. The pGEX-trx-FAST and pGEX-trx-JUN plasmids were transfected into BL21 cells for optimal expression of the GST-trx-FAST and GST-trx-JUN fusion proteins. The fusion proteins were purified by Glutathione-Sepharose chromatography and dialyzed against PBS. We routinely purify approximately 1.5–3.0 mgs. of Trx aptamer fusion protein from a 50° ml culture.

TABLE 8

Primers used to introduce thioredoxin (with Rsr II site) into GST2T vector

| Primer | | Properties |
|---|---|---|
| Trx #1 | 5' cgcggatccatgagcgataaaattattcacc 3' (SEQ ID NO:2) | 5' fwd - Adds N-terminal EcoR1 site (bold) |
| Trx #2 | 5' gcacggaccgcaccactctgc 3' (SEQ ID NO:3) | 3' rev - Adds internal RsrII site (bold) |
| Trx #3 | 5' gtgcggtccgtgcaaaatgatc 3' (SEQ ID NO:4) | 5' fwd - Overlaps #2 at internal RsrII site |
| Trx #4 | 5' ccggaattcctacaggttagcgtcgagg 3' (SEQ ID NO:5) | 3' rev - Add C-terminal BamHI site (bold) |

The PCR product generated with Primers #1 and #2 was annealed with the product generated with Primers #3 and #4 and a second round of PCR was carried out to generate a full length trx gene with a single internal RsrII site at the trx active site and terminal EcoRI and BamHI sites for directional cloning into pGEX2T. The resulting plasmid (pGEX-trx) expressed a 35 kd GST-trx fusion protein in E. coli.

To insert the FAST and c-Jun SIMs into pGEX-trx, overlapping oligonucleotides were synthesized, annealed and extended in a PCR reaction to generate duplex DNA with terminal Rsril sites and a sequence encoding the 24AA SIM from FAST or Jun (Table 9).

Generation of Mutant Peptide Aptamers

Terminal deletion mutations have been generated in the pGEX-trx-FAST aptamers. To generate the deletions, a series of oligonucleotides were synthesized that hybridized to the FAST SIM 2, 4, 6, 8 or 10 codons from either the 5' or 3' end of the FAST SIM (Table 10). The primers included a 5' Ppu M1 site that was used to clone the deleted FAST SIM into the RsrII site (compatible cohesive ends). Briefly, an N-terminal deletion primer was used with the trx4 primer (Table 8) to amplify the FAST SIM missing, for example, the

TABLE 9

Primers used to make the FAST and JUN SIM aptamers

| Primer Sequence | Name | Properties |
|---|---|---|
| 5' gtgtgcggtccgttagatgctttatttcaaggtgttccaccaaacaag 3' (SEQ ID NO:6) | 5' FAST-Fwd | 5' Rsr II site |
| 5' tatgcacggaccgtgatcacgtggatgactaacccaaacatcgtagatactcttgtttggtgg 3' (SEQ ID NO:7) | 3' FAST-Rev | 5' Rsr II site |
| 5' gtgtgcggtccgttaaagcaaaaggttatgaaccatgttaacagtggt 3' (SEQ ID NO:8) | 5' JUN-Fwd | 5' Rsr II site |
| 5' tatgcacggaccgtgaaaggtttgtaattgttgggttaacattaattgacaaccactgttaac 3' (SEQ ID NO:9) | 3' JUN-Rev | 5' Rsr II site |

The pGEX-trx vector was digested with RsrII, treated with Calf Intestinal Phosphatase and gel purified. The FAST and JUN SIM DNAs generated by PCR were digested with RsrII, ligated to the phosphatased vector, and transfected into competent DH5a E. coli cells. Colonies were initially screened for insertion of the SIM DNA into the vector by adding a part of a bacterial colony directly into a PCR reaction mix and amplifying with the trx primers #1 and #4 first two codons through the trx stop codon. The PCR product was digested with Ppu M1 and BamHI and ligated into pGEX-trx vector that had been digested with RsrII and BamHI. The resulting plasmid encoded a trx-SIM-trx fusion protein missing 2 amino acids from the FAST SIM. The mutant plasmids were introduced into BL21 E. coli for expression and purification of the peptide aptamer fusion proteins.

TABLE 10

Oligonucleotide Primers used to generate deletions in the FAST SIM aptamer

| Name | Primer Sequence |
|---|---|
| Δ2-N-terminal | 5' gtggtgtggggtcccgctttatttcaaggtgttcc 3' (SEQ ID NO:10) |
| Δ4-N-terminal | 5' gtggtgtggggtccctttcaaggtgttccaccaaac 3' (SEQ ID NO:11) |
| Δ6-N-terminal | 5' gtggtgtggggtcccggtgttccaccaaacaagag 3' (SEQ ID NO:12) |
| Δ8-N-terminal | 5' gtggtgtggggtccccccaccaaacaagagtatctac 3' (SEQ ID NO:13) |
| Δ10-N-terminal | 5' gtggtgtggggtcccaacaagagtatctacgatgtttg 3' (SEQ ID NO:14) |
| Δ2-C-terminal | 5' gtgtatgcaaggaccttgtggatgactaacccaaacatc 3' (SEQ ID NO:15) |
| Δ4-C-terminal | 5' gtgtatgcaaggaccttgactaacccaaacatcgtagatac 3' (SEQ ID NO:16) |
| Δ6-C-terminal | 5' gtgtatgcaaggaccttgccaaacatcgtagatactcttg 3' (SEQ ID NO:17) |
| Δ8-C-terminal | 5' gtgtatgcaaggaccttgatcgtagatactcttgtttg 3' (SEQ ID NO:18) |
| Δ10-C-terminal | 5' gtgtatgcaaggaccttggatactcttgtttggtggaac 3' (SEQ ID NO:19) |

Characterization of FAST Peptide Aptamer Binding

Figure 6:
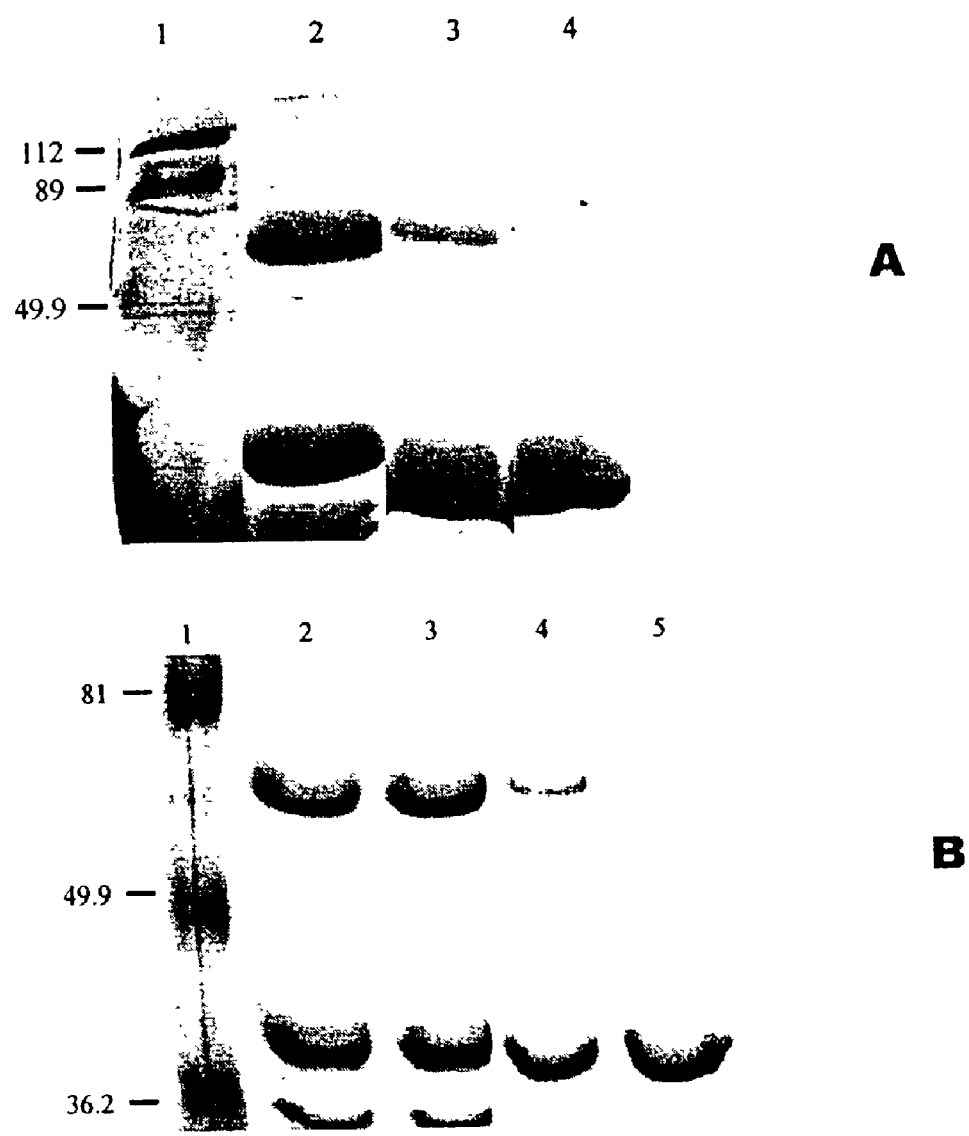
FIGS. 6A and B are a set of photographs of SDS-PAGE stained with commassie blue illustrating that GST-trx aptamers bind Smad2P with specificity in GST pulldown assays of Smad2-P. SDS-PAGE of eluted proteins with Smad-P migrating at ~55 kd and GST fusion proteins at ~38 kd.
FIG. 6B: Lane 1. Molecular Weight Stds. Lane 2. Pulldown of Smad2P with GST-CBP; Lane 3. Pulldown Smad2(H1)P with GST-CBP; Lane 4. Pulldown Smad2P with GST-trx-FAST aptamer; Lane 5. No Pulldown Smad2(H1)P with GST-trx-FAST aptamer. The mutations in Smad2(H1)P disrupt the interaction with the FAST aptamer but not with CBP.

The purified GST-trx-FAST fusion proteins were tested for binding to SmadP proteins by two methods—a GST-pull down assay and the HTRF assay of biotin-FAST peptide binding to Smad2P. For the GST-pulldown, purified GST-trx or GST-trx-FAST protein (5 ug) was mixed with glutathione agarose beads and incubated 1.5 hrs at 4° C. The beads were washed three times with PBS and Smad2P (25 ug) was added for a 1 hr incubation at 4° C. The beads were recovered by centrifugation, washed two times with PBS and eluted by boiling in SDS-Page sample buffer. Proteins were fractionated by SDS-PAGE and visualized after staining with Commassie Blue (FIG. 6). The band at approximately 38 kd is the GST-fusion protein eluted from the beads. As shown in the figure, Smad2P was pulled-out by the beads when GST-trx-FAST protein was present (Lane 3) but not when an unrelated GST-trx protein was present (Lane 4). In the right hand panel of FIG. 6, we show that GST-CBP can pulldown either Smad2-P or Smad2(H1)-P (Lane2 and 3). In contrast, GST-trx-FAST only interacted with Smad2-P (Lane 4) and not with the mutant Smad that is defective in binding FAST.

A more quantitative measure of the GST-trx-FAST binding was obtained by testing its ability to compete for binding to Smad2P with the biotinylated FAST peptide SIM. We used the FAST-SmadP HTRF assay described above. Briefly, His-tagged Smad2P (200 ng), Europium chelate labeled Anti-His tag antibody, 500 nM biotinylated FAST peptide (24 mer) and varying amounts of GST-trx-FAST protein were incubated in a 50 microliter volume in the well of a 384-well black, low-bind microplate. After 1 hr at room temperature, Streptavidin-APC was added to each well and 30 minutes later the fluorescence emissions at 615 nm and 665 nm were read in a PE-Wallac Victor V.

Figure 7:
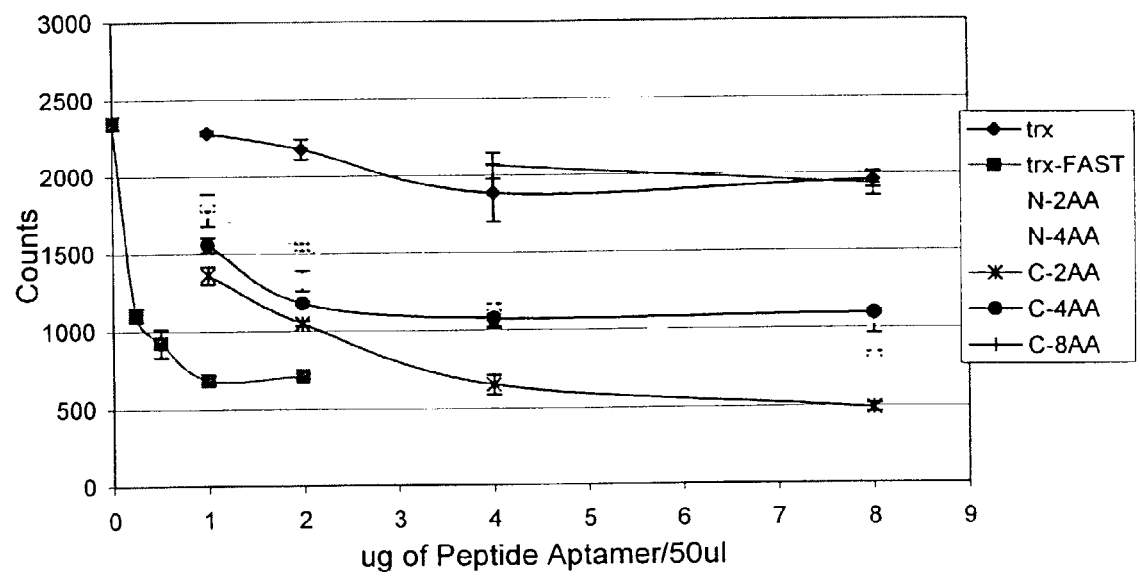
FIG. 7 is a graph illustrating that the HTRF assay for binding Smad interaction motifs to phosphorylated Smad protein can detect changes in binding affinity caused by small deletions in the FAST peptide aptamer.
Figure 8:
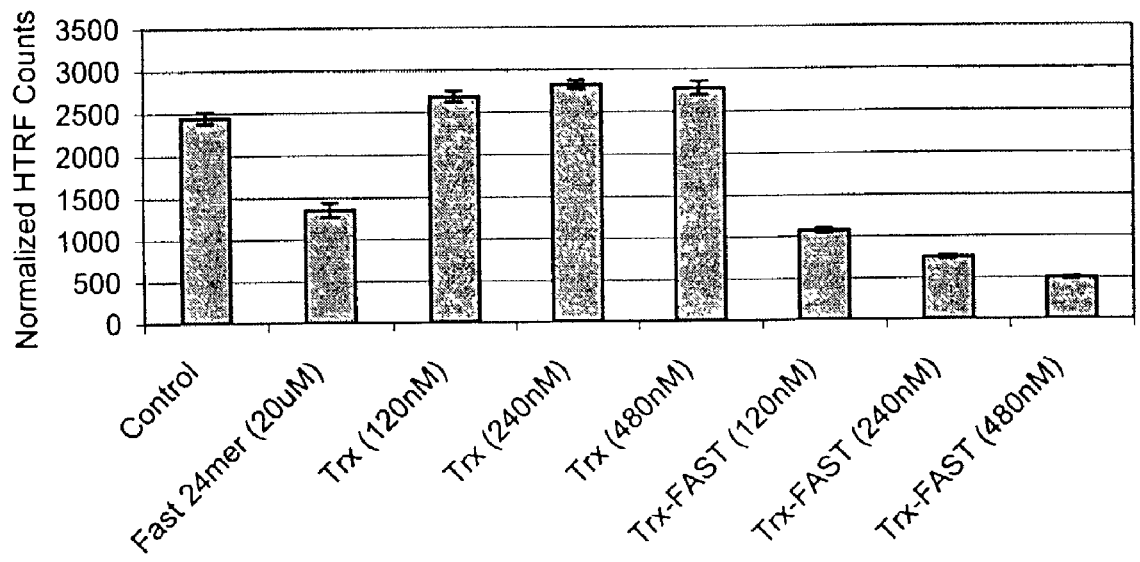
FIG. 8 is a bar graph demonstrating that the HTRF assay for binding to Smad3-P can detect differences in peptide binding affinity. The HTRF assay for detecting Smad protein interactions was used to quantify binding between the FAST Smad interaction motif and purified Smad 3 (phosphorylated). The indicated amounts of peptide or peptide aptamer were added as competitive inhibitors. The thioredoxin (trx) scaffold did not interfere with binding but the trx-FAXT aptamer inhibits at much lower concentrations than did free FAST 24mer peptide.
Figure 9:
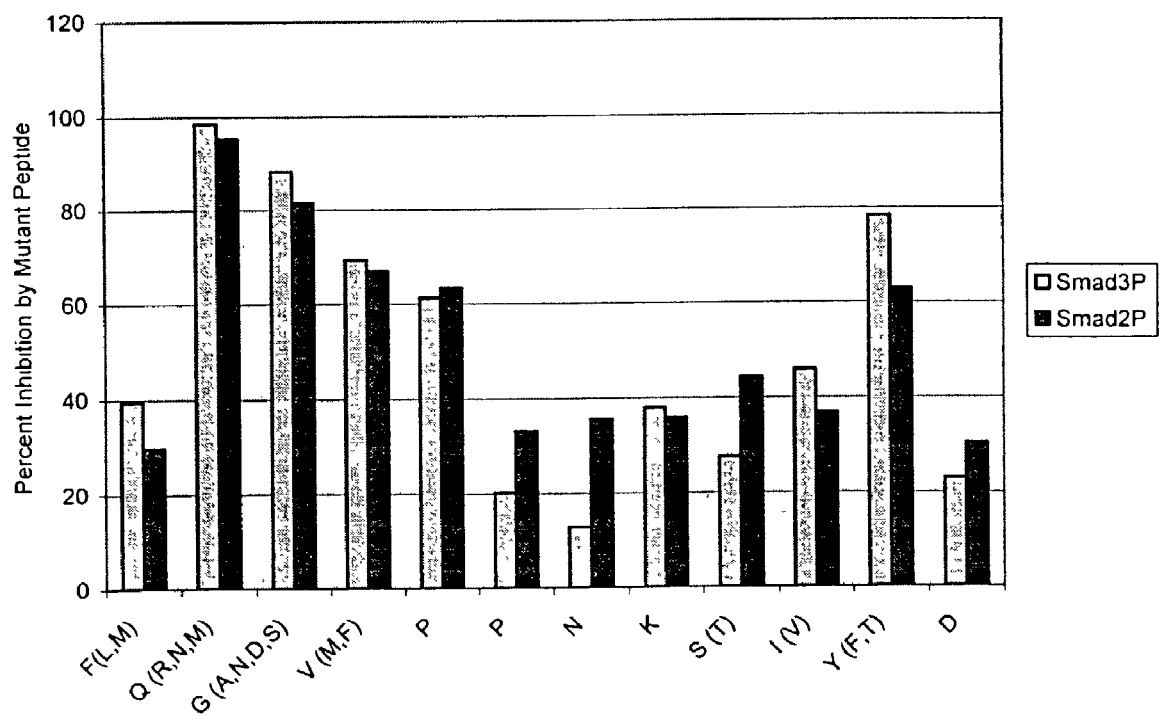
FIG. 9 is a bar graph demonstrating that the HTRF Smad binding assay is sensitive to single amino acid changes in the peptide ligands: effect of alanine substitutions on FAST SIM binding. The HTRF assay for detecting Smad protein interactions was used to quantify binding between the FAST Smad interaction motif and purified Smad 2 or Smad 3 (phosphorylated). GST-Thioredoxin-FAST peptide aptamers were added as competitive inhibitors at 1 ug protein per 50 ul reaction volume. The FAST Smad interaction motif had been mutated by alanine scanning mutagenesis to replace single amino acids with alanine. The inhibitory effects of the mutant peptides were compared to inhibition by the wild type trx-FAST Aptamer. Alanine mutations in the central PPNK (SEQ ID NO:1) reduced the ability of the aptamer to inhibit as did mutation of the phenylalanine (F) toward the N-terminus (left) or the aspartic acid (D) toward the C-terminus (right).

As shown in FIGS. 7 and 8, GST-trx-FAST inhibited binding with an $IC_{50}$ of approximately 250 nM. GST-trx protein at 8 μg/50 ul had very little effect on binding. FIGS. 7 and 8 also show the results with terminal deletions of the FAST SIM in the GST-trx-FAST aptamers. Deletion of only two amino acids from either the N-terminus or the C-terminus of the FAST-SIM resulted in a ~10 fold higher $IC_{50}$, i.e. the deleted aptamers were much poorer inhibitors. Aptamers with larger deletions, e.g., C-8AA, did not inhibit binding of the FAST peptide to Smad-P at the highest concentration tested. The 10-fold increase in the $IC_{50}$ by the 2 amino acid deletions could be due to involvement of those amino acids in binding Smad2P or to an altered conformation of the shorter FAST-SIM. To test the latter hypothesis we will use alanine replacement of amino acids in order to maintain the same length of the SIM on the trx scaffold (FIG. 9).

We claim:

1. A method of screening for selective inhibitors or activators of Smad-target protein binding comprising the steps of:
    (a) obtaining a phosphorylated Smad protein or phosphorylated Smad protein complex,
    (b) allowing the phosphorylated Smad protein or protein complex to interact with a target protein or peptide in the presence of a test compound, and
    (c) analyzing the binding of the phosphorylated Smad protein or protein complex and the target protein or peptide, wherein a perturbation of binding indicates that the test compound is an inhibitor or activator of Smad-target protein interaction and wherein at least 90 samples are analyzed simultaneously.

2. The method of claim 1 wherein the phosphorylated Smad protein comprises a protein selected from the group consisting of Smad2 and Smad3.

3. The method of claim 1 wherein the phosphorylated Smad complex comprises Smad2 and Smad4.

4. The method of claim 1 wherein the target protein is FAST.

5. A method of screening for selective inhibitors or activators of Smad-target protein binding comprising the steps of:
    (a) obtaining a phosphorylated Smad protein or phosphorylated Smad protein complex,
    (b) allowing the phosphorylated Smad protein or protein complex to interact with a target protein or peptide in the presence of a test compound, and
    (c) analyzing the binding of the phosphorylated Smad protein or protein complex and the target protein or peptide, wherein a perturbation of binding indicates that the test compound is an inhibitor or activator of Smad-target protein interaction and wherein step (c) is via homogeneous time resolved fluorescence.

6. A method of screening for selective inhibitors or activators of Smad-target protein binding comprising the steps of:
    (a) obtaining a phosphorylated Smad protein or phosphorylated Smad protein complex,
    (b) allowing the phosphorylated Smad protein or protein complex to interact with a target protein or peptide in the presence of a test compound, and
    (c) analyzing the binding of the phosphorylated Smad protein or protein complex and the target protein or peptide, wherein a perturbation of binding indicates that the test compound is an inhibitor or activator of Smad-target protein interaction, wherein step (c) is via solid phase ELISA assay.

* * * * *